(12) United States Patent
Fallis

(10) Patent No.: US 7,935,836 B2
(45) Date of Patent: May 3, 2011

(54) COMPOUNDS COMPRISING A LINEAR SERIES OF FIVE FUSED CARBON RINGS, AND PREPARATION THEREOF

(76) Inventor: Alexander Graham Fallis, Ottawa (CA)

(*) Notice: Subject to any disclaimer, the term of this patent is extended or adjusted under 35 U.S.C. 154(b) by 119 days.

(21) Appl. No.: 12/536,705

(22) Filed: Aug. 6, 2009

(65) Prior Publication Data

US 2010/0004467 A1 Jan. 7, 2010

Related U.S. Application Data

(63) Continuation-in-part of application No. 11/130,190, filed on May 17, 2005, now Pat. No. 7,655,809.

(60) Provisional application No. 60/571,940, filed on May 18, 2004.

(51) Int. Cl.
*C09B 3/50* (2006.01)
*H01L 51/10* (2006.01)

(52) U.S. Cl. .................. 552/284; 585/422; 257/40

(58) Field of Classification Search ............. 552/284; 257/40; 585/422
See application file for complete search history.

(56) References Cited

U.S. PATENT DOCUMENTS

| | | | |
|---|---|---|---|
| 3,839,034 A | 10/1974 | Wiedemann | |
| 3,871,882 A | 3/1975 | Wiedemann | |
| 3,895,944 A | 7/1975 | Wiedemann et al. | |
| 3,977,870 A | 8/1976 | Rochlitz | |
| 3,989,520 A | 11/1976 | Rochlitz | |
| 4,072,520 A | 2/1978 | Rochlitz et al. | |
| 4,231,799 A | 11/1980 | Rochlitz et al. | |
| 5,141,671 A | 8/1992 | Bryan et al. | |
| 5,151,478 A | 9/1992 | Chiang et al. | |
| 5,151,629 A | 9/1992 | VanSlyke | |
| 5,707,779 A | 1/1998 | Naito | |
| 6,207,472 B1 | 3/2001 | Callegari et al. | |
| 6,284,562 B1 | 9/2001 | Batlogg et al. | |
| 6,344,284 B1 | 2/2002 | Chou | |
| 6,433,359 B1 | 8/2002 | Kelley et al. | |
| 6,452,207 B1 | 9/2002 | Bao | |
| 6,465,116 B1 | 10/2002 | Ishikawa et al. | |
| 6,500,604 B1 | 12/2002 | Dimitrakopoulos et al. | |
| 6,617,609 B2 | 9/2003 | Kelley et al. | |
| 6,682,831 B2 | 1/2004 | Toguchi et al. | |
| 6,690,029 B1 | 2/2004 | Anthony et al. | |
| 6,864,396 B2 | 3/2005 | Smith et al. | |
| 6,963,080 B2 | 11/2005 | Afzali-Ardakani et al. | |
| 6,974,877 B2 | 12/2005 | Vogel et al. | |
| 7,061,010 B2 | 6/2006 | Minakata | |
| 7,125,989 B2 | 10/2006 | Afzali-Ardakani et al. | |
| 7,126,153 B2 | 10/2006 | Iechi et al. | |
| 2001/0015438 A1 | 8/2001 | Callegari et al. | |
| 2003/0097010 A1 | 5/2003 | Vogel et al. | |
| 2003/0116755 A1 | 6/2003 | Takahashi | |
| 2006/0267004 A1* | 11/2006 | Fallis et al. ............ | 257/40 |

FOREIGN PATENT DOCUMENTS

| | | |
|---|---|---|
| CA | 2213240 | 8/1996 |
| CA | 2344084 | 10/2002 |
| CA | 2253654 | 1/2003 |
| EP | 0 726 304 A2 | 8/1996 |
| EP | 0 786 820 A2 | 7/1997 |
| EP | 1 073 993 B2 | 11/2002 |
| GB | 1416603 A | 12/1975 |
| JP | 10158938 A2 | 6/1998 |
| WO | WO 03/016599 A1 | 2/2003 |

OTHER PUBLICATIONS

Ruiz, Ricardo et al., (2003) "Dynamic Scaling, Island Size Distribution, and Morphology in the Aggregation Regime of Submonolayer Pentacene Films", Physical Review Letters, vol. 91, No. 13, pp. 136102-1-136102-4. http://www.ee.princton.edu/~kahnlab/publications/PRL91-136102.pdf.
Ruiz, Ricardo et al., (2003), "Pentacene ultrathin film formation on reduced and oxidized Si surfaces", Physical Review B, vol. 67, Issue 12, pp. 125406-1-125406-7. http://www.ee.princeton.edu/~kahnlab/publications/PRB67-125406.
Koch, N. et al., (2002), "Physisorption-like Interaction at the Interfaces Formed by Pentacene and Samarium", The Journal of Physical Chemistry B, vol. 106, Issue 16, pp. 4192-4196. http://www.ee.princeton.edu/~kahnlab/publications/192.pdf.
Orientation of pentacene films using surface alignment layers and its influence on thin film transistor characteristics http://www.uvm.edu/~rheadric/Reprints/Swiggers2002.pdf.
Gruhn, N.E., et al., (2002) "The Vibrational Reorganization Energy in Pentacene: Molecular Influences on Charge Transport", Journal of the American Chemical Society, vol. 124, Issue 27, pp. 7918-7919. http://www.ee.princeton.edu/~kahnlab/publications/194.pdf.
Synthesis and Application of Pentacene Precursor in OTFT http://www.mrc.utexas.edu/NSFWorkshop/Presentations/afzali1.pdf.
Doped Pentacene Yields Efficient Plastic Solar Cells http://www.photonics.com/spectra/tech/XQ/ASP/techid.828/QX/read.htm.
Physicists from Lucent's Bell Labs devise organic electronics and high-speed communications circuits; win scientific awards http://www.lucent.com/press/0300/000320.bla.html or http://www.globaltechnoscan.com/29march-4thapril/lucent.htm.
Dorsch, Jeff, (2001) "Flexible Electronics: On the Brink of a Tech Revolution", SemiConductor Magazine, Nov. 2001, vol. 2, No. 11. http://dom.semi.org/web/wmagazine.nsf/0/8a7b262af0f00f8c8825-6afb0080dffe?Open Document.

(Continued)

*Primary Examiner* — James O. Wilson
*Assistant Examiner* — Ebenezer Sackey

(57) ABSTRACT

The present application discloses methods for the production of organic compounds comprising a linear series of five fused carbon rings. Such compounds are useful in the production of electronic components, devices and materials. For example the methods disclosed permit the production of 2,9- and 2,10-disubstituted pentacene compounds and 2,6,9,13- and 2,6,10,13-tetrasubstituted compounds that present particularly advantageous properties for the manufacture of semiconductor materials, and may be used in devices such as for example thin film transistors and solar cells. These features are enhanced by π-π parallel stacking in the solid state. Also disclosed are compounds that are excellent candidates for use in the manufacture of semiconductor materials, and other components of electronic systems, by virtue of their solubility, crystal packing geometries, and electronic properties.

20 Claims, No Drawings

OTHER PUBLICATIONS

The Pentacene Project http://www.research.ibm.com/leem/pentacene.html.

Shaw, J.M. and Seidler, P.F., (2001) "Organic Electronics: Introduction", IBM Journal of Research and Development, Jan. 1, 2001, vol. 45, No. 1, pp. 3-9. http://www.findarticles.com/cf_0/m3125/10_72/62657296/print.jhtml.

IBM Scientists Take Significant Step Toward Production of Flexible Electronics http://www.findarticles.com/cf_0/m0WVI/2000_Nov_6/66810932/print.jhtml.

Park, J.H.; Kang, C.H.; Kim, Y.J.; Lee, Y.S. and Choi, J.S., (2004) "Characteristics of pentacene-based thin-film transistors", Materials Science and Engineering: C (Elsevier Science), vol. 24, No. 1, pp. 27-29, (Abstract).

Kim, K.; Yoon, Y.K.; Mun, M.-O.; Park, S.P.; Kim, S.S.; IM, S. and Kim, J.H., (2002) "Optical Properties of Solid Pentacene", Journal of Superconductivity: Incorporating Novel Magnetism (Kluwer Academic Publishers), vol. 15, No. 6, pp. 595-598.

Senadeera, G.K.R.; Jayaweera, P.V.V.; Perera, V.P.S. and Tennakone, K., (2002) "Solid-state dye-sensitized photocell based on pentacene as a hole collector", Solar Energy Materials and Solar Cells (Elsevier Science), vol. 73, No. 1, pp. 103-108.

Guaino, P.; Cafolla, A.A.; Carty, D.; Sheerin, G. and Hughes, G., (2003) "An STM investigation of the interaction and ordering of pentacene molecules on the Ag/Si(111)-(3x3)R30 surface", Surface Science (Elsevier Science), vol. 540, No. 1, pp. 107-116.

Brillante, A.; Della Valle, R.G.; Farina, L.; Girlando, A.; Masino, M. and Venuti, E., (2002) "Raman phonon spectra of pentacene polymorphs", Chemical Physics Letters (Elsevier Science), vol. 357, No. 1, pp. 32-36.

Mattheus, C.C.; Dros, A.B., Baas, J.; Oostergetel, G.T.; Meetsma, A.; De Boer, J.L. and Palstra, T.T.M., (2003) "Identification of polymorphs of pentacene", Synthetic Metals (Elsevier Science), vol. 138, No. 3, pp. 475-481.

De Wijs, G.A.; Mattheus, C.C.; De Groot, R.A. and Palstra, T.T.M., (2003) "Anisotropy of the mobility of pentacene from frustration", Synthetic Metals (Elsevier Science), vol. 139, No. 1, pp. 109-114.

Salih, A.J. and Marshall, J.M., (1997) "High-mobility low-threshold-voltage pentacene thin-film transistors prepared at rapid growth rates of pulsed-laser deposition", Philosophical Magazine Letters (Taylor and Francis Ltd.), Mar. 1, 1997, vol. 75, No. 3, pp. 169-177.

Menozzi, C.; Corradini, V.; Cavallini, M.; Biscarini, F.; Betti, M.G. and Mariani, C., (2003) "Pentacene self-aggregation at the Au(110)-(1x2) surface: growth morphology and interface electronic states", Thin Solid Films (Elsevier Science), Mar. 20, 2003, vol. 428, Issues 1-2, pp. 227-231.

Lee, Y.S.; Park, J.H. and Choi, J.S., (2003) "Electrical characteristics of pentacene-based Schottky diodes", Optical Materials (Elsevier Science), vol. 21, No. 1, pp. 433-437.

Pedash, Y.F.; Prezhdo, O.V.; Kotelevskiy, S.I. and Prezhdo, V.V., (2002) "Spin-orbit coupling and luminescence characteristics of conjugated organic molecules. I. Polyacenes", Journal of Molecular Structure: THEOCHEM (Elsevier Science), vol. 585, No. 1, pp. 49-59.

Afzali, A., et al., (2002) "High-Performance, Solution-Processed Organic Thin Film Transistors from a Novel Pentacene Precursor", Journal of the American Chemical Society, vol. 124, Issue 30, pp. 8812-8813.

Afzali, A., et al., (2003) "Photosensitive Pentacene Precursor: Synthesis, Photothermal Patterning, and Application in Thin-Film Transistors", Advanced Materials, vol. 15, Issue 24, pp. 2066-2069.

Anthony, J.E., et al., (2002) "A Road Map to Stable, Soluble, Easily Crystallized Pentacene Derivatives", Organic Letters, vol. 4, No. 1, pp. 15-18.

Aubry, J.-M.; Pierlot, C.; Rigaudy, J.; Schmidt, R., (2003) "Reversible binding of oxygen to aromatic compounds", Accounts of Chemical Research, vol. 36, No. 9, pp. 668-675.

Collins, S.K., et al., (2000) "The Synthesis of a Novel Strained Diyneparacyclophane and Its Dimer by Metal-Mediated Coupling", Angewandte Chemie International Edition, vol. 39, No. 2, pp. 385-388.

Collins, S.K., et al., (2000) "Synthesis of Novel Acetylenic Cyclophanes with Helical Chirality: Potential New Structures for Liquid Crystals", Organic Letters, vol. 2, No. 20, pp. 3189-3192.

Collins, S.K., et al., (2002) "A Novel Strained Undecadiyne Cyclophane with Interesting Dienophilic Character", Organic Letters, vol. 4, No. 1, pp. 11-14.

Cory, R.M.; McPhail, C.L.; Dikmans, A.J., (1993) "Linearly fused ribbons of carbocyclic six-membered rings via Diels-Alder cycloadditions 1. Model studies and key intermediates", Tetrahedron Letters, Nov. 19, 1993, vol. 34, No. 47, pp. 7533-7536.

Danishefsky, S.J.; Kitahara, T.; Yan, C.F.; Morris, J., (1979) "Diels-Alder Reactions of trans-1-Methoxy-3-trimethylsilyloxy-1,3-butadiene", Journal of the American Chemical Society, vol. 101, No. 23, pp. 6996-7000.

Danishefsky, S.J.; Yan, C.F.; Singh, R.K.; Gammill, R.B.; McCurry, P.; Fritsch, N.; Clardy, J.C., (1979) "Derivatives of 1-Methoxy-3-trimethylsilyloxy-1,3-butadiene for Diels-Alder Reactions", Journal of the American Chemical Society, vol. 101, No. 23, pp. 7001-7008.

Gelinck, G.H. et al., (2004) "Flexible active-matrix displays and shift registers based on solution-processed organic transistors", Nature Materials, vol. 3, Feb. 2004, pp. 106-110.

Goodings, E.P. et al., (1972) "Synthesis, structure, and electrical properties of naphthacene, pentacene, and hexacene sulphides", Journal of the Chemical Society, Perkin Transactions 1, pp. 1310-1314.

Hendrickson, J.B. and Bergeron, R., (1973) "Triflamides: new acylating and triflating reagents", Tetrahedron Letters, vol. 14, No. 46, pp. 4607-4610.

Heuft, M.A. et al., (2001) "Synthesis of Diynes and Tetraynes from in Situ Desilylation/Dimerization of Acetylenes", Organic Letters, vol. 3, No. 18, pp. 2883-2886.

Heuft, M.A. and Fallis, G., (2002) "Template-directed synthesis of helical phenanthroline cyclophanes", Angewandte Chemie International Edition, Dec. 2002, vol. 41, No. 23, pp. 4520-4523.

Heuft, M.A. et al., (2003) "Molecular Folding of C60 Acetylenic Cyclophanes: π-Stacking of Superimposed Aromatic Rings", Organic Letters, vol. 5, No. 11, pp. 1911-1914.

Ito, K. et al., (2003) "Oligo(2,6-anthrylene)s: acene-oligomer approach for organic field-effect transistors", Angewandte Chemie International Edition, Mar. 10, 2003, vol. 42, No. 10, pp. 1159-1162.

Katz, H.E. et al., (2001) "Synthetic Chemistry for Ultrapure, Processable, and High-Mobility Organic Transistor Semiconductors", Accounts of Chemical Research, vol. 34, No. 5, pp. 359-369.

Li, G. and Shinar, J., (2003) "Combinatorial fabrication and studies of bright white organic light-emitting devices based on emission from rubrene-doped 4,4'-bis(2,2'-diphenylvinyl)-1,1'-biphenyl", Applied Physics Letters, Dec. 29, 2003, vol. 83, No. 26, pp. 5359-5361.

Meyer Zu Heringdorf, F.-J. et al., (2001) "Growth dynamics of pentacene thin films", Nature, Aug. 2, 2001, vol. 412, pp. 517-520.

Morris, J.L. et al., (1994) "Synthesis of Extended Linear Aromatics Using Tandem Diels-Alder Aromatization Reactions", The Journal of Organic Chemistry, vol. 59, Issue 21, pp. 6484-6486, (Abstract).

Randic, M., (2003) "Aromaticity of Polycyclic Conjugated Hydrocarbons", Chemical Reviews, vol. 103, No. 9, pp. 3449-3602.

Schuster, I.I.; Craciun, L.; Ho, D.M.; Pascal, R.A. Jr., (2002) "Synthesis of a strained, air-sensitive, polycyclic aromatic hydrocarbon by means of a new 1,4-benzadiyne equivalent", Tetrahedron, Oct. 21, 2002, vol. 58, Issue 43, pp. 8875-8882.

Schleyer, P.R. et al., (2001) "The Acenes: Is There a Relationship between Aromatic Stabilization and Reactivity?", Organic Letters, vol. 3, No. 23, pp. 3643-3646.

Takahashi, T. et al., (2000) "Straightforward Method for Synthesis of Highly Alkyl-Substituted Naphthacene and Pentacene Derivatives by Homologation", Journal of the American Chemical Society, vol. 122, No. 51, pp. 12876-12877.

Patent Abstracts of Japan, 10-158938, "Method for Applying Oil to Elastic Fiber", Jun. 16, 1998, Matsumoto Yushi Seiyaku Co. Ltd.

\* cited by examiner

COMPOUNDS COMPRISING A LINEAR SERIES OF FIVE FUSED CARBON RINGS, AND PREPARATION THEREOF

CROSS REFERENCE TO RELATED APPLICATION

This application is a continuation-in-part of prior U.S. patent application Ser. No. 11/130,190 filed on May 17, 2005 which claims the priority right of prior U.S. patent application Ser. No. 60/571,940 filed on May 18, 2004 by applicants herein.

FIELD OF THE INVENTION

The present invention relates to the field of pentacene compounds. More specifically, the present invention relates to compounds comprising a linear series of five fused carbon rings (e.g. 2,9- and 2,10-disubstituted pentacenes), their production and use in semiconductor materials and organic thin film electronic devices. The present invention also provides direct routes from a common synthetic intermediate Diels-Alder adduct to both p-type and n-type pentacene semiconductors with variable substituted core structures if desired. Pentacene is an example of a versatile semiconductor platform that may be synthesized to generate either p-type or n-type properties by controlling the electron density of the acene ring. Pentacene itself is a p-type semiconductor but perfluoropentacene is a n-type semiconductor.

BACKGROUND TO THE INVENTION

Semiconductors are materials that have electronic properties between electrical insulators and electrical conductors. The efficiency of a semiconducting material is determined by how easily the electrons and electron 'holes' can move through the material—i.e. the electron and hole mobilities ($\mu_e$ or $\mu_h$). Highly conjugated organic compounds have overlapping atomic orbitals that form valence and conducting bands similar to metals. Organic semiconductors do not have the same electron or hole mobilities as single-crystalline silicon, but they are advantageous during fabrication as solution processing techniques such as lithography can be used. Silicon and gallium arsenide semiconductors, silicon dioxide insulators, and metals such as aluminum and copper have dominated the semiconductor industry for many years. More recently, however, organic thin-film transistors (OTFTs) have presented an alternative to the traditional thin-film transistors based on inorganic materials. For example, research efforts have focused on linear acenes (including tetracene and pentacene), thiophene oligomers (including α-sexithiophene), regioregular polythiophenes, copper phthalocyanines and naphthalenebisimides as candidates for organic semiconductors (Katz H. E. et al. *Acc Chem Res* (2001), 34, 359). Of these, pentacene exhibits the best electron and hole mobilities. Charge-carrier mobility values of 1.5 $cm^2V^{-1}s^{-1}$, on/off current ratios greater than $10^8$, and sub-threshold voltages of less than 1.6 V have been reported for pentacene-based transistors. Therefore, the charge-carrier mobility values for pentacenes are comparable or even superior to those of amorphous silicon-based devices.

A rapid two-step synthesis for pentacene was reported in 1972, as shown in Scheme 1, and pentacene was found to be both light and air sensitive (Goodings E. P. et al. *J Chem Soc, Perkin I* (1972), 1310). However, more problematic is the virtual insolubility of pentacene in common organic solvents, thereby preventing solution-based processing (Mayer zu Heingdorf F.-J. et al. *Nature* (2001) 412, 517). As a result, pentacene must generally be deposited from the vapor phase by vacuum sublimation in order to achieve maximum performance. The vacuum sublimation method, however, requires expensive equipment and lengthy pump-down cycles.

Scheme 1: A synthesis of pentacene

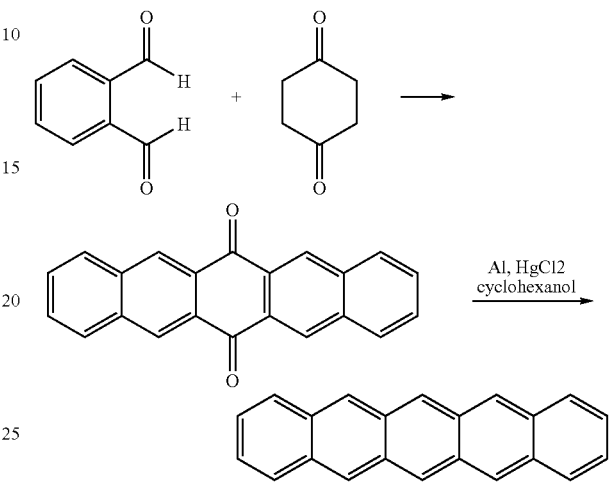

Another disadvantage of pentacene relates to its polymorphic nature, which can have a detrimental influence upon the performance and reproducibility of pentacene-based devices. The alignment or structural order of the pentacene molecules differs for each polymorph or crystallographic phase, and this structural order determines the electronic properties of the device. The crystallographic phase adopted by pentacene depends on the method and conditions under which the crystals are formed. For example, when pentacene is vapor-deposited onto a substrate, a thin film phase is formed. This thin film phase is more effective at transporting charge than pentacene's bulk or single crystal phase, but it is meta-stable. For example, the thin film form of pentacene can be converted to the bulk phase by exposure to solvents such as isopropanol, acetone or ethanol.

More recently, substituted pentacene compounds have been developed that are more soluble in organic solvents, exhibit regular crystal packing, and are better suited for organic processing. For example, corresponding international patent publications WO03/028125, and WO03/027050, both published Apr. 3, 2003 and which are incorporated herein by reference, disclose substituted pentacene compounds and methods for their preparation. The substitutions include electron-donating groups and halogen atoms. Such petancene compounds are, at least in selected embodiments, suited for use in organic semiconductor materials. Particularly useful semiconductor compounds include 2,9- and 2,10-disubstituted pentacenes, which are predicted to exhibit excellent solubility, solid-state packing and π-orbital overlap (Anthony, J. E. et al. *J Am Chem Soc* (2001), 123, 9482; Anthony J. E. et al. *Org Lett* (2002) 4, 15).

To date, the production of 2,9- and 2,10-disubstituted pentacenes has been difficult to achieve. International patent publication WO03/027050 discloses a method for preparing pentacene derivatives comprising the step of cyclizing at least one substituted bis(benzyl)phthalic acid to form the corresponding substituted pentacenedione by using an acid composition comprising trifluoromethanesulphonic acid, wherein the bis(benzyl)phthalic acid is selected from:

Scheme 2: A different synthesis of pentacene

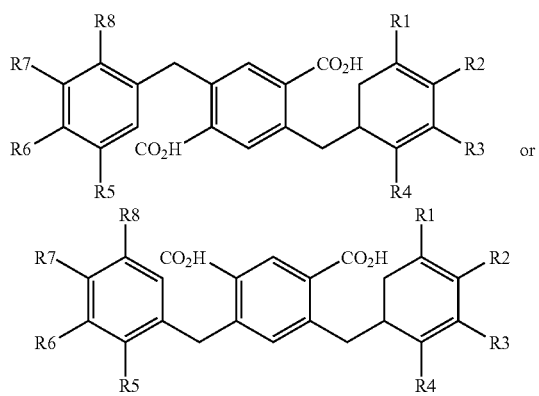

each R representing an electron-donating group, a halogen atom, or a hydrogen atom. In selected embodiments, the method is suitable for generating a 2,9- or 2,10-disubstituted pentacene 5,7 or 5,12-dione, which can undergo reduction and dehydration to generate the corresponding disubstituted pentacene.

There remains a continuing need to develop novel pathways for the production of compounds comprising a linear series of five fused carbon rings, such as for example 2,9- and 2,10-disubstituted pentacene compounds, and corresponding pentacene derivatives. Moreover, there remains a need to develop methods that are better suited for large-scale production of a broad range of pentacene derivatives, and other compounds comprising a linear series of five fused carbon rings, within minimal cost. New pathways are desired to present opportunities to develop new classes of pentacene derivatives, for example with alternative substitutions either on the A and E rings, or the other rings such as C of the five fused carbon rings core structure. Recent review articles describe the rapid progress plus significant international research interest that pentacenes semiconductors continue to receive. (Bendikov, M. et al., *Chem. Rev.*, (2004), 104, 4891; Anthony, J. E., *Chem. Rev.* (2006), 106, 5028; Anthony, J. E., *Angew. Chem. Int. Ed.*, (2008), 47, 452)

SUMMARY OF THE INVENTION

It is one object of the present invention, at least in selected embodiments, to provide a method for producing compounds comprising a core structure including a linear series of five fused carbon rings.

It is another object of the present invention, at least in selected embodiments, to provide intermediates suitable for use in the production of pentacene derivatives with one or more substitutions on the A and/or the C and/or the E rings.

It is another object of the present invention, at least in selected embodiments, to provide compounds suitable for use in electronic devices, for example in thin film transistors, or for other use as a semiconductor, or for use in inkjet fabrication.

It is another object of the present invention to provide novel compounds comprising a linear series of five fused carbon rings including, but not limited to, novel pentacenes.

Certain exemplary embodiments provide a method for the preparation of a compound comprising at least one linear series of five fused carbon rings, the method comprising the steps of:
(a) providing a compound containing at least one quinone moiety;
(b) providing an unsubstituted or substituted acyclic, cyclic or heterocyclic diene;
(c) performing a double or stepwise cycloaddition reaction between the compound containing the quinone moiety and the diene to generate a carbonyl substituted core structure comprising five fused carbon rings sequentially identified as rings A, B, C, D, and E of general formula V, and optionally comprising additional substituents:

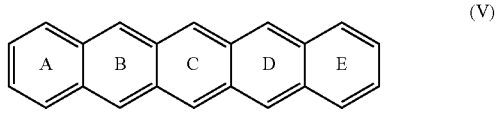

Other exemplary embodiments provide a method for the preparation of a compound comprising at least one linear series of five fused carbon rings, the method comprising the steps of:
(a) providing an unsubstituted or substituted quinone of the general formula Ib:

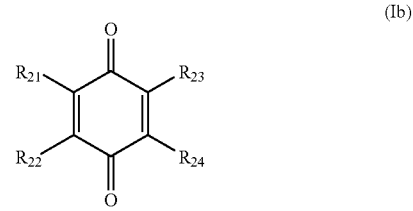

wherein each of $R_{21}$, $R_{22}$, $R_{23}$, and $R_{24}$ is independently selected from the group consisting of hydrogen, an electron-withdrawing group, halo, a trialkylsilyl, a trialkylsilylalkynyl, an alkoxy, an aryloxy, and an amine;
(b) providing an unsubstituted or substituted acyclic diene of the general formula IIb:

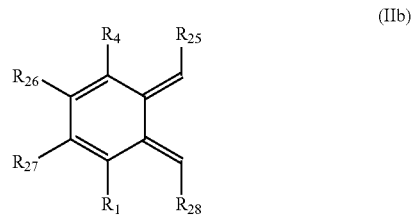

wherein each of $R_1$, $R_4$, $R_{25}$, $R_{26}$, $R_{27}$, and $R_{28}$ is independently selected from the group consisting of hydrogen, an electron-withdrawing group, halo, a trialkylsilyl, a trialkylsilylalkynyl, an alkoxy, an aryloxy, and an amine;
(c) performing a double or stepwise cycloaddition reaction between the quinone and the diene to generate a core structure comprising five fused carbon rings sequentially identified as rings A, B, C, D, and E;
(d) optionally replacing or adding selected substituents;
to generate a product of general formula IV, wherein each R group is independently selected from the group consisting of hydrogen, alkyl, alkenyl, alkynyl, aryl, a heterocycle, an electron-withdrawing group, halo, trifluoromethylsulfonyl, alkoxy, aryloxy, amine, haloalkyl, trialkylsilyl, trialkylsilylalkynyl, a thienyl group and a perfluorothienyl group that is unsubstituted or substituted with an alkyl, perfluoroalkyl, alkenyl, alkynyl, halo, haloalkyl, trialkylsilyl, trialkylsilylalkynyl, or a combination thereof:

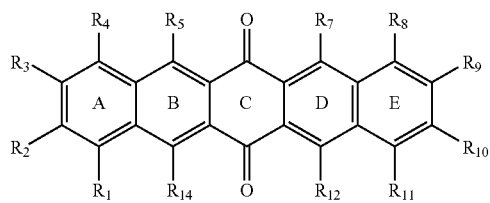

(IV)

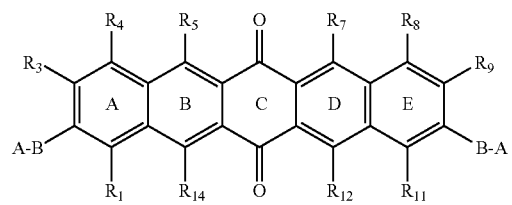

(IVb)

wherein these steps may be performed in any order.

Yet other exemplary embodiments can provide a method for the preparation of a pentacene comprising substitutions at least at the 2 position, and at one of the 9 or 10 position, the method comprising the steps of:

(a) performing a stepwise or double Diels-Alder reaction or an equivalent reaction by reacting a compound of formula IIb with a compound of formula Ib:

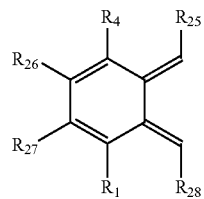

(IIb)

wherein one of $R_{26}$ or $R_{27}$ comprises A-B, A is a protective group, B is a group to be protected, and each R group is independently selected from the group consisting of hydrogen, an electron-withdrawing group, halo, a trialkylsilyl, trialkylsilylalkynyl, an alkoxy, an aryloxy, and an amine;

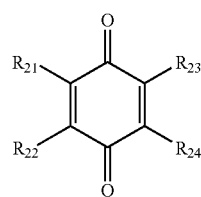

(Ib)

(b) replacing or adding selected substituents wherein each R group is independently selected from a group consisting of hydrogen, an electron-withdrawing group, halo, a trialkylsilyl, a trialkylsilylalkynyl, an alkoxy, an aryloxy, and an amine; wherein the method generates compounds of formula IVa and/or formula IVb:

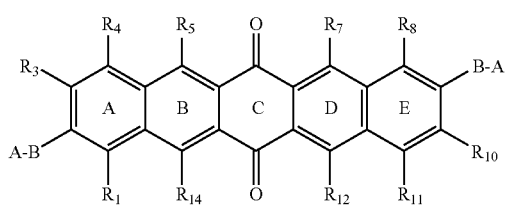

(IVa)

wherein A is a protective group, B is a group to be protected, and each R group is independently selected from the group consisting of hydrogen, alkyl, alkenyl, alkynyl, aryl, a heterocycle, an electron-withdrawing group, halo, trifluoromethylsulfonyl, alkoxy, aryloxy, amine, haloalkyl, trialkylsilyl, trialkylsilylalkynyl, a thienyl group and a perfluorothienyl group that is unsubstituted or that is substituted with an alkyl, perfluoroalkyl, perfluoroalkanylperfluorothienyl, alkenyl, alkynyl, halo, haloalkyl, trialkylsilyl, trialkylsilylalkynylthienyl, or a combination thereof; in which these steps may be performed in any order;

(c) optionally separating the compounds of formula (IVa) and formula (IVb), and selecting the compound of formula (IVb) and/or the compound of formula (IVa) for further processing in which these steps may be performed in any order;

(d) optionally replacing each A or each A-B with an alternative substituent, with or without a linker comprising one or more triple bonds to form a 2,9- and/or a 2,10-disubstituted quinone;

(e) optionally subjecting the 2,9- and/or the 2,10-disubstituted quinone of formula (IVb) and/or the compound of formula (IVa) to reducing/condensation/aromatization conditions to generate a pentacene compound of formula (Vb) and/or a pentacene compound of formula (Va);

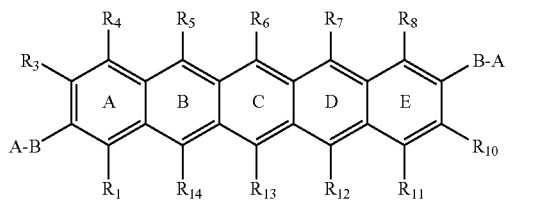

(Va)

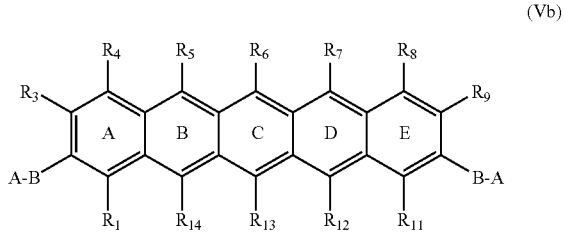

(Vb)

substituted at least in the 2 position, and one of the 9 or 10 position, wherein the substitutents from $R_1$ to $R_{14}$ are each independently selected from the group consisting of hydrogen, alkyl, alkenyl, alkynyl, aryl, a heterocycle, an electron-withdrawing group, a conjugated electron-withdrawing group, dicyanomethyl, halo, trifluoromethylsulfonyl, alkoxy, aryloxy, amine, haloalkyl, trialkylsilyl, trialkylsilylalkynyl, a thienyl group and a perfluorothienyl group that is unsubstituted or substituted with an alkyl, perfluoroalkyl, alkenyl, alkynyl, halo, haloalkyl, trialkylsilyl, trialkylsilylalkynyl, or a combination thereof, in which these steps may be performed in any order; and (f) optionally subjecting the 2,9- and/or the 2,10-disubstituted quinone of formula (IVb) and/or the compound of formula (IVa) to reducing/condensation/aromatization conditions to generate a pentacene of formula (V):

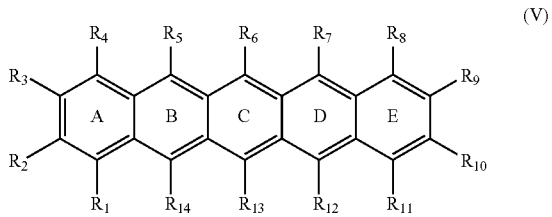

(V)

wherein $R_2$, and one of $R_9$ or $R_{10}$ are A-B, and each remaining R group is independently selected from the group consisting of hydrogen, alkyl, alkenyl, alkynyl, aryl, a heterocycle, an electron-withdrawing group, a conjugated electron-withdrawing group, dicyanomethyl, halo, trifluoromethylsulfonyl, alkoxy, aryloxy, amine, haloalkyl, trialkylsilyl, trialkylsilylalkynyl, a thienyl group and a perfluorothienyl that is unsubstituted or substituted with an alkyl, perfluoroalkyl, alkenyl, alkynyl, halo, haloalkyl, trialkylsilyl, trialkylsilylalkynyl, or a combination thereof, in which these steps may be performed in any order.

Through significant inventive ingenuity, the inventors of the present invention have developed novel methods for the synthesis of organic compounds comprising for example a linear series of five fused carbon rings. Such compounds may include, but are not limited to, anthradiquinones, quinones and pentacenes. The methods of the present invention permit facile access to a broad range of compounds comprising the aforementioned five-fused carbon ring core. Such compounds include, for example, pentacenes, which may include a broad range of substituents. For example, the inclusion of acetylene groups (or at least substitutions comprising acetylene linkers) on the A and E rings affords access to compounds that are particularly suited to electronic applications. Moreover, such compounds are amenable to further manipulation, for example to custom design pentacenes having optimal electronic properties. The novel compounds of the present invention are suitable for use in the manufacture of numerous types of electronic devices, including for example thin film transistors and solar cells.

DEFINITIONS

Numbering Scheme for Pentacenes

Compounds with fused aromatic ring systems are commonly given a numbering sequence in which each carbon atom that is amenable to substitution is numbered. (See, for example, James E. Banks, NAMING ORGANIC COMPOUNDS: A PROGRAMMED INTRODUCTION TO ORGANIC CHEMISTRY, Saunders College Publishing, p. 124, PA (1976).) The numbering sequence that is generally used for pentacene, for example, is shown below.

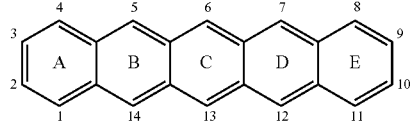

The location of a substituent on such a compound is commonly specified by reference to the number of the carbon atom to which the substituent is bonded. There is one hydrogen atom bonded to each numbered carbon atom if no substituent is indicated. In general, the rings are identified by a letter A, B, C, and so on as shown above.

Linear Series of Five Fused Carbon Rings:

This expression refers to all compounds comprising a core structure having five fused carbon rings arranged in a linear series. Such compounds include, but are not limited to anthradiquinones, quinines, and pentacenes. Each ring of such compounds may independently be saturated, unsaturated, or aromatic, and be unsubstituted or substituted.

For convenience, the numbering scheme for substituents of all compounds comprising a linear series of five fused carbon rings is generally based upon the pentacene core structure (as discussed above) throughout this specification. However, renumbering of corresponding R groups on products (compared to corresponding substrates) does not necessarily infer that the substituent has been replaced.

Reduction/Reducing/Condensation/Aromatization Conditions:

The term "reduction" or "reducing conditions" refers to any form of reaction that results in (i) the acceptance of one or more electrons by an atom or ion, (ii) the removal of oxygen from a compound, or the addition of hydrogen to a compound. In the context of this application, the terms further encompass reactions involving alcohols, as intermediates, such as, for example, Grignard reactions, base mediated condensation reactions, including for example reduction/addition to a carbonyl group to generate an alcohol. The terms include addition to generate an alcohol intermediate, which may be followed by aromatization.

Protective Group:

This expression encompasses any form of protective group, including for example those described in Green, T. W. and Wuts P. G. M., "Protective Groups in Organic Synthesis" ($3^{rd}$ ed. 1999) published by John Wiley ad Sons Inc. Optionally, the protective groups of the present invention are encompassed by A-B, wherein A is a protective group and B is a group to be protected. A-B can include, but is not limited to, OSi, OH, OTf, OTs, OMs, ONs, NSi, and acetylene groups, or groups comprising a linker have at least one triple carbon-carbon bond. A-B therefore includes OH (wherein H can be considered a form of "protecting group"). In selected embodiments, when B (the group to be protected) includes O or N then A can be silyl, hydrogen or sulfonate, alkyl, perfluoroalkyl, or aryl. In other selected embodiments, where B includes a carbon or hetero atom, then A can be silyl, hydrogen or sulfonate alkyl, perfluoroalkyl or aryl.

Preferred/Optionally:

Unless otherwise stated, the terms "preferred" and "optionally" refer only to preferred features or aspect of the invention over the broadest embodiments of the invention.

Acetylene:

Acetylene groups encompass, at least in selected embodiments, any group comprising at least one triple carbon bond, or a group comprising a linker comprising at least one triple carbon bond.

Additional Chemical Terms

The term "carbo", "carbyl," "hydrocarbon" and "hydrocarbyl," as used herein, pertain to compounds and/or groups which have only carbon and hydrogen atoms.

The term "hetero," as used herein, pertains to compounds and/or groups which have at least one heteroatom, for example, multivalent heteroatoms (which are also suitable as ring halide) such as boron, silicon, nitrogen, phosphorus, oxygen, and sulfur, and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "ring," as used herein, pertains to a closed ring of from 3 to 10 covalently linked atoms, more optionally 3 to 8 covalently linked atoms.

The term "aromatic ring," as used herein, pertains to a closed ring of from 3 to 10 covalently linked atoms, more optionally 5 to 8 covalently linked atoms, which ring is aromatic.

The term "heterocyclic ring," as used herein, pertains to a closed ring of from 3 to 10 covalently linked atoms, more optionally 3 to 8 covalently linked atoms, wherein at least one of the ring atoms is a multivalent ring heteroatom, for example, nitrogen, phosphorus, silicon, oxygen, and sulfur, though more commonly nitrogen, oxygen, and sulfur.

The term "perfluoro heterocyclic ring," as used herein, pertains to a closed ring of from 3 to 10 covalently linked atoms, more optionally 3 to 8 covalently linked atoms, wherein at least one of the ring atoms is a multivalent ring heteroatom, for example, nitrogen, phosphorus, silicon, oxygen, and sulfur, though more commonly nitrogen, oxygen, and sulfur. Perfluoro indicates that all hydrogen substitutents have been replaced by fluorine substitutents.

The term "alicyclic," as used herein, pertains to compounds and/or groups which have one ring, or two or more rings (e.g., spiro, fused, bridged), wherein said ring(s) are not aromatic.

The term "aromatic," as used herein, pertains to compounds and/or groups which have one ring, or two or more rings (e.g., fused), wherein at least one of said ring(s) is aromatic.

The term "perfluoro-heterocyclic," as used herein, indicates that all hydrogen substituents have been replaced by fluorine substituents, and also pertains to cyclic compounds and/or 10 groups which have one heterocyclic ring, or two or more heterocyclic rings (e.g., spiro, fused, bridged), wherein said ring(s) may be alicyclic or aromatic.

The term "heterocyclic," as used herein, pertains to cyclic compounds and/or 10 groups which have one heterocyclic ring, or two or more heterocyclic rings (e.g., spiro, fused, bridged), wherein said ring(s) may be alicyclic or aromatic.

The term "heteroaromatic," as used herein, pertains to cyclic compounds and/or groups which have one heterocyclic ring, or two or more heterocyclic rings (e.g., 15 fused), wherein said ring(s) is aromatic.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

In one selected embodiment, the substituent(s) are independently selected from: halo; hydroxy; ether (e.g., $C_{1-7}$alkoxy); formyl; acyl (e.g., $C_{1-7}$alkylacyl, $C_{5-20}$ arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., $C_{1-7}$haloalkyl, $C_{1-7}$hydroxyalkyl, $C_{1-7}$-carboxyalkyl, $C_{1-7}$aminoalkyl, $C_{5-20}$aryl-$C_{1-7}$alkyl); $C_{3-20}$heterocyclyl; or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

In one selected embodiment, the substituent(s) are independently selected from:
—F, —Cl, —Br, and –1;
—OH;
—OMe, —OEt, —O(tBu), and —OCH$_2$Ph;
—SH;
—SMe, —SEt, —S(tBu), and —SCH$_2$Ph;
—C(=O)H;
—C(=O)Me, —C(=O)Et, —C(=O)(tBu), and —C(=O)Ph;
—C(=O)OH;
—C(=O)OMe, —C(=O)OEt, and —C(=O)O(tBu);
=CH—C(=O)OMe, =C—[C(=O)OMe]$_2$, =CH—C(=O)OEt, and =C—[C(=O)OEt]$_2$,
—C(=O)NH$_2$, —C(=O)NHMe, —C(=O)NMe$_2$, and —C(=O)NHEt;
—NHC(=O)Me, —NHC(=O)Et, —NHC(=O)Ph, succinimidyl, and maleimidyl;
—NH$_2$, —NHMe, —NHEt, —NH(iPr), —NH(nPr), —NMe$_2$, —NEt$_2$, —N(iPr)$_2$, —N(nPr)$_2$, —N(nBU)$_2$, and —N(tBu)$_2$;
—CN;
=CHCN and =C(CN)$_2$
—NO$_2$;
=CHNO$_2$ and =C(NO$_2$)$_2$
-Me, -Et, -nPr, -iPr, -nBu, -tBu; —CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$;
—CH$_2$OH, —CH$_2$CH$_2$OH, and —CH(OH)CH$_2$OH;
—CH$_2$NH$_2$, CH$_2$CH$_2$NH$_2$, and —CH$_2$CH$_2$NMe$_2$; and, optionally substituted phenyl.

The substituents are described in more detail below.

$C_{1-7}$alkyl: The term "$C_{1-7}$alkyl," as used herein, pertains to a monovalent moiety obtained by removing a hydrogen atom from a $C_{1-7}$hydrocarbon compound having from 1 to 7 carbon atoms, which may be aliphatic or alicyclic, or a combination thereof, and which may be saturated, partially unsaturated, or fully unsaturated.

Examples of (unsubstituted) saturated linear $C_{1-7}$alkyl groups include, but are not limited to, methyl, ethyl, n-propyl, n-butyl, n-pentyl (amyl), and the perfluorinated analogs.

Examples of (unsubstituted) saturated branched $C_{1-7}$alkyl groups include, but are not limited to, iso-propyl, iso-butyl, sec-butyl, tert-butyl, and neo-pentyl.

Examples of saturated alicyclic (also carbocyclic) $C_{1-7}$alkyl groups (also referred to as "$C_{3-7}$cycloalkyl" groups) include, but are not limited to, unsubstituted groups such as cyclopropyl, cyclobutyl, cyclopentyl, cyclohexyl, and norbornane, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of (unsubstituted) unsaturated $C_{1-7}$alkyl groups which have one or more carbon-carbon double bonds (also referred to as "$C_{2-7}$ alkenyl" groups) include, but are not limited to, ethenyl (vinyl, —CH=CH$_2$), 2-propenyl (allyl, —CH—CH=CH$_2$) isopropenyl (—C(CH$_3$)=CH$_2$), butenyl, pentenyl, and hexenyl.

Examples of (unsubstituted) unsaturated groups with one carbon-carbon double bond (referred to as methylenes =CH$_2$)

Examples of (substituted) conjugated unsaturated groups have one more carbon-carbon double bonds attached, one or more electron-withdrawing group may also be attached (such as carbonyl, cyano, ester, carboxylic acid, etc.) (referred to as vinylcyano (=CHCN), disubstituted compounds as dicyanomethyl (=C(CN)$_2$) or as dicyanovinyl (=C(CN)$_2$), or as dienmalonitrile, (=C(CN)$_2$), while tetracyano compounds from para-quinones may be named tetracyano-p-quinodimethanes (TCNQ)

Examples of (unsubstituted) unsaturated $C_{1-7}$alkyl groups which have one or more carbon-carbon triple bonds (also referred to as "$C_{2-7}$alkynyl" groups) include, but are not limited to, ethynyl, and 2-propynyl (propargyl).

Examples of unsaturated alicyclic (also carbocyclic) $C_{1-7}$alkyl groups which have one or more carbon-carbon double bonds (also referred to as "$C_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

Additional examples of substituted $C_{3-7}$cycloalkyl groups include, but are not limited to, those with one or more other rings fused thereto, for example, those derived from: indene ($C_9$), indan (2,3-dihydro-1H-indene) ($C_9$), tetraline (1,2,3,4-tetrahydronaphthalene) ($C_{10}$), adamantane ($C_{10}$), decalin (decahydronaphthalene) ($C_{12}$), fluorene ($C_{13}$), phenalene ($C_{13}$). For example, 2H-inden-2-yl is a $C_5$cycloalkyl group with a substituent (phenyl) fused thereto.

$C_{3-20}$heterocyclyl: The term "$C_{3-20}$heterocyclyl," as used herein, pertains to a monovalent moiety obtained by removing a hydrogen atom from a ring atom of a $C_{3-20}$heterocyclic compound, said compound having one ring, or two or more rings (e.g., spiro, fused, bridged), and having from 3 to 20 ring atoms, of which from 1 to 10 are ring heteroatoms, and wherein at least one of said ring(s) is a heterocyclic ring. Optionally, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms.

For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{3-7}$heterocyclyl, $C_{5-7}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$) piperidine ($C_6$) dihydropyridine ($C_6$), tetrahydropyridine ($C_6$), azepine ($C_7$);

—$O_1$: oxirane ($C_3$) oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_6$), and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

$C_{5-20}$ aryl: The term "$C_{5-20}$ aryl," as used herein, pertains to a monovalent moiety obtained by removing a hydrogen atom from an aromatic ring atom of a $C_{5-20}$aromatic compound, said compound having one ring, or two or more rings (e.g., fused), and having from 5 to 20 ring atoms, and wherein at least one of said ring(s) is an aromatic ring. Optionally, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. This particularly applied to substituents of the pentacene core of the compounds generated in accordance with the present invention.

For example, the term "$C_{5-6}$aryl," as used herein, pertains to an aryl group having 5 or 6 ring atoms. Examples of groups of aryl groups include $C_{3-20}$aryl, $C_{5-7}$aryl, $C_{5-6}$aryl.

The ring atoms may be all carbon atoms, as in "carboaryl groups" (e.g., $C_{5-20}$carboaryl).

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), pyrene ($C_{16}$), and fullerenes particularly for example $C_{60}$ ("Bucky Ball") such as $C_{60}H$ or $C_{60}R_{100}$, wherein $R_{100}$ represents any substituent, particularly those discussed herein. Indeed, 2,9 and 2,10 disubstituted pentacenes substituted with fullerene groups generate dumbbell-shaped molecules that may have particular use in specific embodiments.

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, including but not limited to oxygen, nitrogen, and sulfur, as in "heteroaryl groups." In this case, the group may conveniently be referred to as a "$C_{5-20}$heteroaryl" group, wherein "$C_{5-20}$" denotes ring atoms, whether carbon atoms or heteroatoms. Optionally, each ring has from 5 to 7 ring atoms, of which from 0 to 4 are ring heteroatoms.

Examples of monocyclic heteroaryl groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heterocyclic groups (some of which are also heteroaryl groups) which comprise fused rings, include, but are not limited to:

$C_9$heterocyclic groups (with 2 fused rings) derived from benzofuran ($O_1$), isobenzofuran ($O_1$), indole ($N_1$), isoindole ($N_1$), purine ($N_4$) (e.g., adenine, guanine), benzimidazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$heterocyclic groups (with 2 fused rings) derived from benzodioxan ($O_2$), quinoline ($N_1$), isoquinoline ($N_1$), benzoxazine ($N_1O_1$), benzodiazine ($N_2$), pyridopyridine ($N_2$) quinoxaline ($N_2$) quinazoline ($N_2$);

$C_{13}$heterocyclic groups (with 3 fused rings) derived from carbazole ($N_1$), dibenzofuran ($O_1$), dibenzothiophene ($S_1$); and, $C_{14}$heterocyclic groups (with 3 fused rings) derived from acridine ($N_1$), xanthene ($O_1$), phenoxathiin ($O_1S_1$), phenazine ($N_2$) phenoxazine ($N_1O_1$), phenothiazine ($N_1S_1$), thianthrene ($S_2$), phenanthridine ($N_1$), phenanthroline ($N_2$) phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)=(also denoted —N$^+$(→O$^-$)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms. Monocyclic examples of such groups include, but are not limited to, those derived from:

$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$)(e.g., cytosine), pyrimidinedione (CO (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:

$C_9$: indenedione;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$);
$N_4$: purinone ($C_9$) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride ($C_5$), succinic anhydride ($C_5$), and glutaric anhydride ($C_6$);

cyclic carbonates (—O—C(=O)—O— in a ring), such as ethylene carbonate ($C_5$) and 1,2-propylene carbonate ($C_5$);

imides (—C(=O)—NR—C(=O)— in a ring), including but not limited to, succinimide ($C_5$), maleimide ($C_5$), phthalimide, and glutarimide ($C_6$);

lactones (cyclic esters, —O—C(=O)— in a ring), including, but not limited to, β-propiolactone, γ-butyrolactone, δ-valerolactone (2-piperidone), and ∈-caprolactone;

lactams (cyclic amides, —NR—C(=O)— in a ring), including, but not limited to, β-propiolactam ($C_4$), γ-butyrolactam (2-pyrrolidone) ($C_5$), δ-valerolactam ($C_6$) and ∈-caprolactam ($C_7$);

cyclic carbamates (—O—C(=O)—NR— in a ring), such as 2-oxazolidone ($C_5$);

cyclic ureas (—NR—C(=O)—NR— in a ring), such as 2-imidazolidone ($C_5$) and pyrimidine-2,4-dione (e.g., thymine, uracil) ($C_6$).

The above $C_{1-7}$alkyl, $C_{3-20}$heterocyclyl, and $C_{5-20}$aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and –1.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), optionally a $C_{1-7}$alkyl group.

$C_{1-7}$alkoxy: —OR, wherein R is a $C_{1-7}$alkyl group. Examples of $C_{1-7}$alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ∈-caprolactone; and lactams (cyclic amides, —NH—C(=O)— in a ring), including, but not limited to, β-propiolactam, γ-butyrolactam, δ-valerolactam, and ∈-caprolactam.

Imino (imine): =NR, wherein R is an imino substituent, for example, hydrogen, $C_{1-7}$alkyl group, a $C_{3-20}$heterocyclyl group, or a $C_{5-20}$aryl group, optionally hydrogen or a $C_{1-7}$alkyl group. Examples of imino groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), optionally a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Acylhalide (haloformyl, halocarbonyl): —C(=O)X, wherein X is —F, —Cl, —Br, or –1, optionally —Cl, —Br, or Carboxy (carboxylic acid): —COOH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, optionally a $C_{1-7}$alkyl group. Examples of ester groups include, but are not limited to, —C(=O)OCH$_3$, —C(=O)OCH$_2$CH$_3$, —C(=O)OC(CH$_3$)$_3$, and C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, optionally a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)NH(CH$_3$)$_2$, —C(=O)NHCH$_2$CH$_3$, and —C(=O)N(CH$_2$CH$_3$)$_2$, as well as amido groups in which R$^1$ and R$^2$ together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, a $C_{1-7}$alkyl group, a $C_{3-20}$heterocyclyl group, or a $C_{5-20}$aryl group, optionally a $C_{1-7}$alkyl group, and R$^2$ is an acyl substituent, for example, a $C_{1-7}$alkyl group, a $C_{3-20}$heterocyclyl group, or a $C_{5-20}$aryl group, optionally a $C_{1-17}$alkyl group. Examples of acylamido groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

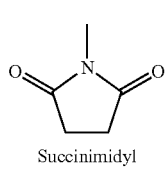
Succinimidyl

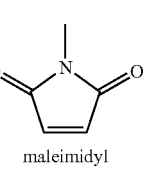
maleimidyl

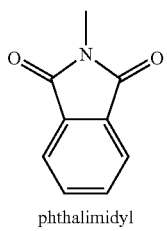
phthalimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)NH(CH$_3$)$_2$, and —C(=S)NHCH$_2$CH$_3$.

Tetrazolyl: a five membered aromatic ring having four nitrogen atoms and one carbon atom,

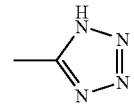

Diazine, including 1,3 diazine, pyrimidine, miazine.

Amino: —NR$^1$R$^2$, wherein R$^1$ and R$^2$ are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, optionally H or a $C_{1-7}$alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh.

Examples of cyclic amino groups include, but are not limited to, aziridino, azetidino, piperidino, piperazino, morpholino, and thiomorpholino.

Nitro: —NO$_2$

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, optionally a $C_{1-7}$alkyl group. Examples of $C_{1-7}$alkylthio groups include, but are not limited to, —SCH$_3$ and —SCH$_2$CH$_3$.

Sulfonic acid (sulfo): —S(=O)$_2$OH.

Sulfonate (sulfonic acid ester): —S(=O)$_2$OR, wherein R is a sulfonate substituent, for example, a $C_{1-7}$alkyl group, a $C_{3-20}$heterocyclyl group, or a $C_{5-20}$aryl group, optionally a $C_{1-7}$alkyl group. Examples of sulfonate groups include, but are not limited to, —S(=O)2OCH$_3$ and —S(=O)2OCH$_2$CH$_3$.

Sulfone (sulfonyl): —S(=O)$_2$R, wherein R is a sulfone substituent, for example, a $C_{1-7}$alkyl group, a $C_{3-20}$heterocyclyl group, or a $C_{5-20}$aryl group, optionally a $C_{1-7}$alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Sulfonyloxy: —OS(=O)$_2$R, wherein R is a sulfonyloxy substituent, for example, a $C_{1-7}$alkyl group, a $C_{3-20}$heterocyclyl group, or a $C_{5-20}$aryl group, optionally a $C_{1-7}$alkyl group. Examples of sulfonyloxy groups include, but are not limited to, —OS(=O)$_2$CH$_3$ and —OS(=O)$_2$CH$_2$CH$_3$.

Sulfinyl: —S=O

Sulfinyloxy: —OS(=O)R, wherein R is a sulfinyloxy substituent, for example, a $C_{1-7}$alkyl group, a $C_{3-20}$heterocyclyl group, or a $C_{5-20}$aryl group, optionally a $C_{1-7}$alkyl group.

Examples of sulfinyloxy groups include, but are not limited to, —OS(=O)CH$_3$ and —OS(=O)CH$_2$CH$_3$.

Sulfamino: —NR$^1$S(=O)$^2$OH, wherein R$^1$ is an amino substituent, as defined for amino groups. Examples of sulfamino groups include, but are not limited to, —NHS(=O)$^2$OH and —N(CH$^3$)S(=O)$^2$)H.

Sulfonamino: —NR$^1$S(=O)$^2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, optionally a C$_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$alkyl group, a C$_{3-20}$heterocyclyl group, or a C$_{5-20}$aryl group, optionally a C$_{1-7}$alkyl group. Examples of sulfinamino groups include, but are not limited to, —NHS(=O)CH3 and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido: —S(=O)$_2$NR$^1$R$^2$ wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

As mentioned above, a C$_{1-7}$alkyl group may be substituted with, for example, hydroxy (also referred to as a C$_{1-7}$hydroxyalkyl group), C$_{1-7}$alkoxy (also referred to as a C$_{1-7}$alkoxyalkyl group), amino (also referred to as a C$_{1-7}$aminoalkyl group), halo (also referred to as a C$_{1-7}$haloalkyl group), carboxy (also referred to as a C$_{1-7}$carboxyalkyl group), and C$_{5-20}$aryl (also referred to as a C$_{5-20}$aryl-C$_{1-7}$alkyl group).

Similarly, a C$_{5-20}$aryl group may be substituted with, for example, hydroxy (also referred to as a C$_{5-20}$hydroxyaryl group), halo (also referred to as a C$_{5-20}$haloaryl group), amino (also referred to as a C$_{5-20}$aminoaryl group, e.g., as in aniline), C$_{1-7}$alkyl (also referred to as a C$_{1-7}$alkyl-C$_{5-20}$aryl group, e.g., as in toluene), and C$_{1-7}$alkoxy (also referred to as a C$_{1-7}$alkOXY—C$_{5-20}$aryl group, e.g., as in anisole).

These and other specific examples of such substituted groups are also discussed below.

C$_{1-7}$haloalkyl group: The term "C$_{1-7}$haloalkyl group," as used herein, pertains to a C$_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a C$_{1-7}$perhaloalkyl group." Examples of C$_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

C$_{1-7}$hydroxyalkyl: The term "C$_{1-7}$hydroxyalkyl group," as used herein, pertains to a C$_{1-7}$alkyl group in which at least one hydrogen atom has been replaced with a hydroxy group. Examples of C$_{1-7}$hydroxyalkyl groups include, but are not limited to, —CH$_2$OH, —CH$_2$CH$_2$OH, and —CH(OH)CH$_2$OH.

C$_{1-7}$carboxyalkyl: The term "C$_{1-7}$carboxyalkyl group," as used herein, pertains to a C$_{1-7}$alkyl group in which at least one hydrogen atom has been replaced with a carboxy group. Examples of C$_{1-7}$carboxyalkyl groups include, but are not limited to, —CH$_2$COOH and —CH$_2$CH$_2$COOH.

C$_{1-7}$aminoalkyl: The term "C$_{1-7}$aminoalkyl group," as used herein, pertains to a C$_{1-7}$alkyl group in which at least one hydrogen atom has been replaced with an amino group. Examples of C$_{1-7}$aminoalkyl groups include, but are not limited to, —CH$_2$NH$_2$, —CH$_2$CH$_2$NH$_2$, and —CH$_2$CH$_2$N(CH$_3$)$_2$.

C$_{1-7}$alkyl-C$_{5-20}$aryl: The term "C$_{1-7}$alkyl-C$_{5-20}$aryl," as used herein, describes certain C$_{5-20}$aryl groups which have been substituted with a C$_{1-7}$alkyl group. Examples of such groups include, but are not limited to, tolyl (as in toluene), xylyl (as in xylene), mesityl (as in mesitylene), styryl (as in styrene), and cumenyl (as in cumene).

C$_{5-20}$aryl-C$_{1-7}$alkyl: The term "C$_{5-20}$aryl-C$_{1-7}$alkyl," as used herein, describes certain C$_{1-7}$alkyl groups which have been substituted with a C$_{5-20}$aryl group. Examples of such groups include, but are not limited to, benzyl (phenylmethyl), tolylmethyl, phenylethyl, and triphenylmethyl (trityl).

C$_{5-20}$haloaryl: The term "C$_{5-20}$haloaryl," as used herein, describes certain C$_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Bidentate Substituents

Some substituents are bidentate, that is, have two points for covalent attachment. For example, a bidentate group may be covalently bound to two different atoms on two different groups, thereby acting as a linker therebetween. Alternatively, a bidentate group may be covalently bound to two different atoms on the same group, thereby forming, together with the two atoms to which it is attached (and any intervening atoms, if present) a cyclic or ring structure. In this way, the bidentate substituent may give rise to a heterocyclic group/compound and/or an aromatic group/compound. Typically, the ring has from 3 to 8 ring atoms, which ring atoms are carbon or heteroatoms (e.g., boron, silicon, nitrogen, phosphorus, oxygen, and sulfur, typically nitrogen, oxygen, and sulfur), and wherein the bonds between said ring atoms are single or double bonds, as permitted by the valencies of the ring atoms. Typically, the bidentate group is covalently bound to vicinal atoms, that is, adjacent atoms, in the parent group.

C$_{1-7}$alkylene: The term "C$_{1-7}$alkylene," as used herein, pertains to a bidentate moiety obtained by removing two hydrogen atoms, either both from the same carbon atom, or one from each of two different carbon atoms, of a C$_{1-7}$hydrocarbon compound having from 1 to 7 carbon atoms, which may be aliphatic or alicyclic, or a combination thereof, and which may be saturated, partially unsaturated, or fully unsaturated.

Examples of linear saturated C$_{1-7}$alkylene groups include, but are not limited to, —(CH$_2$)$_n$— where n is an integer from 1 to 7, for example, —CH$_2$— (methylene), —CH$_2$CH$_2$— (ethylene), —CH$_2$CH$_2$CH$_2$— (propylene), and —CH$_2$CH$_2$CH$_2$CH$_2$— (butylene).

Examples of branched saturated C$_{1-7}$alkylene groups include, but are not limited to, —CH(CH$_3$)—, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{1-7}$alkylene groups include, but are not limited to, —CH=CH— (vinylene), —CH=CH—CH2-, —CH=CH—CH$_2$—CH$_2$—, —CH=CH—CH$_2$—CH$_2$—CH$_2$—, —CH=CH—

—CH═CH—, —CH═CH—CH═CH—CH$_2$—, —CH═CHCH═CH—CH$_2$—CH$_2$—, —CH═CH—CH$_2$—CH═CH—, and —CH═CH—CH$_2$—CH$_2$—CH═CH—.

Examples of branched partially unsaturated C$_{1-7}$alkylene groups include, but are not limited to, —C(CH$_3$)═CH—, —C(CH$_3$)═CH—CH$_2$—, and —CH═CH—CH(CH$_3$)—.

Examples of alicyclic saturated C$_{1-7}$alkylene groups include, but are not limited to, cyclopentylene (e.g., cyclopent-1,3-ylene), and cyclohexylene (e.g., cyclohex-1,4ylene).

Examples of alicyclic partially unsaturated C$_{1-7}$alkylene groups include, but are not limited to, cyclopentenylene (e.g., 4-cyclopenten-1,3-ylene), cyclohexenylene (e.g., 2-cyclohexen-1,4-ylene, 3-cyclohexen-1,2-ylene, 2,5-cyclohexadien-1,4-ylene).

C$_{5-20}$arylene: The term "C$_{5-20}$arylene," as used herein, pertains to a bidentate moiety obtained by removing two hydrogen atoms, one from each of two different ring atoms of a C$_{5-20}$aromatic compound, said compound having one ring, or two or more rings (e.g., fused), and having from 5 to 20 ring atoms, and wherein at least one of said ring(s) is an aromatic ring. Optionally, each ring has from 5 to 7 ring atoms.

The ring atoms may be all carbon atoms, as in "carboarylene groups," in which case the group may conveniently be referred to as a "C$_{5-20}$carboarylene" group.

Alternatively, the ring atoms may include one or more heteroatoms, including but not limited to oxygen, nitrogen, and sulfur, as in "heteroarylene groups." In this case, the group may conveniently be referred to as a "C$_{5-20}$heteroarylene" group, wherein "C$_{5-20}$" denotes ring atoms, whether carbon atoms or heteroatoms. Optionally, each ring has from 5 to 7 ring atoms, of which from 0 to 4 are ring heteroatoms.

Examples of C$_{5-20}$arylene groups which do not have ring heteroatoms (i.e., C$_{5-20}$carboarylene groups) include, but are not limited to, those derived from benzene (i.e., phenyl) (C$_6$), naphthalene (C$_{10}$), anthracene (C$_{14}$), phenanthrene (C$_{14}$), and pyrene (C$_{16}$).

Examples of C$_{5-20}$heteroarylene groups include, but are not limited to, C$_5$heteroarylene groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and C$_6$heteroarylene groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

C$_{5-20}$Arylene-C$_{1-7}$alkylene: The term "C$_{5-20}$arylene-C$_{1-7}$alkylene," as used herein, pertains to a bidentate moiety comprising a C$_{5-20}$arylene moiety, -Arylene-, linked to a C$_{1-7}$alkylene moiety, -Alkylene-, that is, -Arylene-Alkylene-.

Examples of C$_{5-20}$arylene-C$_{1-7}$alkylene groups include, but are not limited to, phenylene-methylene, phenylene-ethylene, phenylene-propylene, and phenylene-ethenylene (also known as phenylene-vinylene).

C$_{5-20}$Alkylene-C$_{1-7}$arylene: The term "C$_{5-20}$alkylene-C$_{1-7}$arylene," as used herein, pertains to a bidentate moiety comprising a C$_{5-20}$alkylene moiety, -Alkylene-, linked to a C$_{1-7}$arylene moiety, -Arylene-, that is, -Alkylene-Arylene-.

Examples of C$_{5-20}$alkylene-C$_{1-7}$arylene groups include, but are not limited to, methylene-phenylene, ethylene-phenylene, propylene-phenylene, and ethenylene-phenylene (also known as vinylene-phenylene).

Included in the above are the well known ionic, salt, solvate (e.g., hydrate), and protected forms of these substituents. For example, a reference to carboxylic acid (—COOH) also includes carboxylate (—COO$^-$). Similarly, a reference to an amino group includes a salt, for example, a hydrochloride salt, of the amino group. A reference to a hydroxyl group also includes conventional protected forms of a hydroxyl group. Similarly, a reference to an amino group also includes conventional protected forms of an amino group.

In particularly selected embodiments of the invention, the term 'substituents' may include but is not limited to the group consisting of hydrogen, C$_2$-C$_{20}$ alkenyl, C$_2$-C$_{20}$ alkynyl, C$_1$-C$_{20}$ alkyl, aryl, C$_1$-C$_{20}$ carboxylate, C$_1$-C$_{20}$ alkoxy, C$_2$-C$_{20}$ alkenyloxy, aryloxy, C$_2$-C$_{20}$ alkoxycarbonyl, C$_1$-C$_{20}$ alkylthio, C$_1$-C$_{20}$ alkylsulfonyl, or C$_1$-C$_{20}$ alkylsulfinyl; each optionally substituted with C$_1$-C$_5$ alkyl, halogen, C$_1$-C$_5$ alkoxy, or with a phenyl group optionally substituted with halogen, C$_1$-C$_5$ alkyl, or C$_1$-C$_5$ alkoxy, and acetylene comprising from 2 to 20 carbon atoms. In specific embodiments acetylene substituents may be particularly preferred. In other selected embodiments, each substituent may be a metallocycles or heterocyclicmetallocycles (to include porphyrins and phthalocyaines), or perfluoroalkyl or diazine, attached either directly to the linear series of five fused carbon rings, or attached via acetylene. Each substituent is selected independently to other substituents unless otherwise indicated.

DETAILED DESCRIPTION OF THE INVENTION

Functionalized pentacene compounds with substituents on the terminal A and E rings are predicted to have better intermolecular π-stacking than compounds with substituents attached to the central C ring. However, few synthetic routes to pentacenes with substituents on the A and E rings are currently known. Pentacene has a greater electron density and reactivity at the central C ring (Schleyer P. R. et al. *Org Lett* (2001) 3, 3646; Randić M. *Chem Rev* (2003) 103, 3449) making selective functionalization of pentacene on the A and E rings difficult.

In selected embodiments, the inventors have developed novel pathways for the production of compounds comprising a linear series of five fused carbon rings, which are believed to present significant advantages over the methods of the prior art. Without wishing to be bound by theory, the methods present the opportunity to manufacture, at least in selected embodiments, alternative pentacene substitutions at the A, C, and E rings, thereby providing a greater degree of substituent flexibility. Such substituents can be used to more carefully tune the electronic properties and/or affect the solid-state packing of the pentacene derivatives for use in electronic components such as thin-film transistors. However, the invention is not limited in this regard. The methods permit the formation of a wide range of compounds with a core structure comprising a linear series of five fused carbon rings. The novel methods allow facile access to a wide range of compounds including substituted pentacenes, pentacene-quinones, bis(cyanomethyl)-p-pentacenes and anthradiquinones that were previously unobtainable or difficult to obtain.

Such compounds include those of formula III and IV and V:

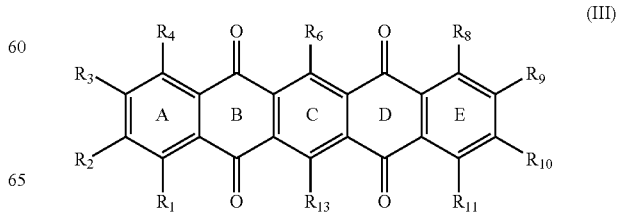
(III)

-continued

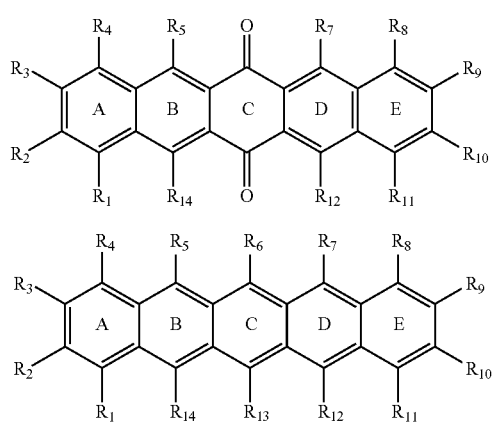

wherein $R_1$, to $R_{14}$ are each independently unsubstituted or substituted. The methods, at least in selected embodiments, allow access to compounds comprising at least one substituent on each of the A and E rings of the core structure, or compounds comprising at least one substituent on each of the A and E rings, and at least one substituent on at least one of the B, C, or D rings of the core structure. The methods also allow access to compounds with substitutions at the 2, and the 9 or 10 positions, plus substitutions at the 6 and 13 positions as well as other positions in the five fused carbon rings system.

In one particularly selected embodiment of the present invention there is provided a method for the preparation of a compound comprising at least one linear series of five fused carbon rings, each carbon ring being saturated, unsaturated, or aromatic, and being unsubstituted or substituted, the method comprising the steps of:
(a) providing an unsubstituted or substituted 1,4,5,8-anthradiquinone or unsubstituted or substituted quinone;
(b) providing an unsubstituted or substituted acyclic diene;
(c) performing a double or stepwise cycloaddition reaction between the 1,4,5,8-anthradiquinone or quinone and the diene compound to generate a core structure comprising five fused carbon rings;
(d) optionally performing an aromatization reaction or equivalent on the A, B, C, D, and E rings of the core structure;
(e) optionally replacing or adding selected substituents;
(f) optionally subjecting the compound to reducing/condensation/aromatization conditions to generate a corresponding unsubstituted or substituted pentacene;
(g) optionally separating isomeric products; and
(h) optionally performing a coupling reaction to link two or more core structures;
wherein optional steps (d), (e), (f), (g), and (h), can be performed in any order.

In selected embodiments the 1,4,5,8-anthradiquinone has the general formula Ia and the quinone has the general formula Ib:

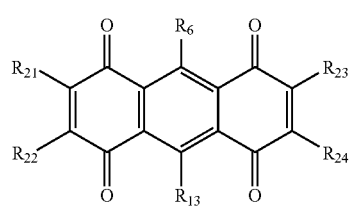

-continued

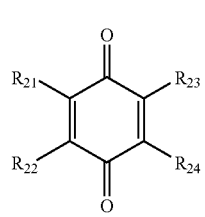

wherein each R group is independently selected from the group consisting of an electron-withdrawing group, halogen, and an amine. Moreover, the diene compound has the general formula IIa or IIb:

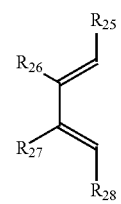

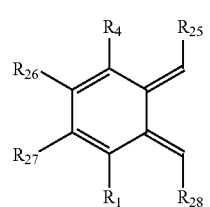

wherein each R group is independently selected from the group consisting of hydrogen, an electron-withdrawing group, halo, a trialkylsilyl, trialkylsilylalkynyl, an alkoxy, an aryloxy, or an amine. A group is selected that does not interfere with the capacity of the diene to undergo a cycloaddition reaction with 1,4,5,8-anthradiquinone, or quinone. Optionally the reaction comprises a double Diels-Alder reaction between the anthradiquinone or quinone and two diene molecules. In selected embodiments, $R_{25}$ may be considered a leaving group. For example, $R_{25}$ may comprise OAlk wherein each Alk comprises an alkyl group of from 1 to 12 carbon atoms.

In specific embodiments of the invention, use of dienes of the formula IIb results in the production of linear five-fused carbon rings structure in the manner shown in Scheme 2 below:

Scheme 3: Cycloaddition route to substituted pentacene quinones

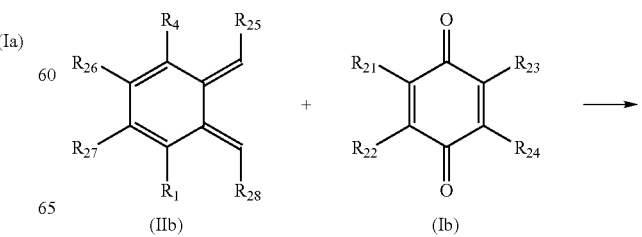

-continued

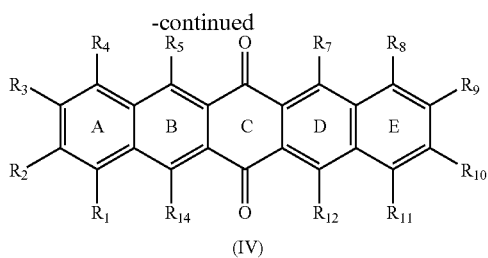

(IV)

The adduct may be aromatized directly by reduction, or preferentially, by a more useful synthetic variant, by a condensation-elimination reaction, and/or by addition of hydride or an organometallic reagent followed by treatment of the alcohol product directly with a Lewis Acid. This may be conducted in the manner shown in Scheme 3 below, in which the intermediates do not have to be isolated, unless desired.

Scheme 4: Reduction/Condensation/Aromatization route to substituted pentacenes

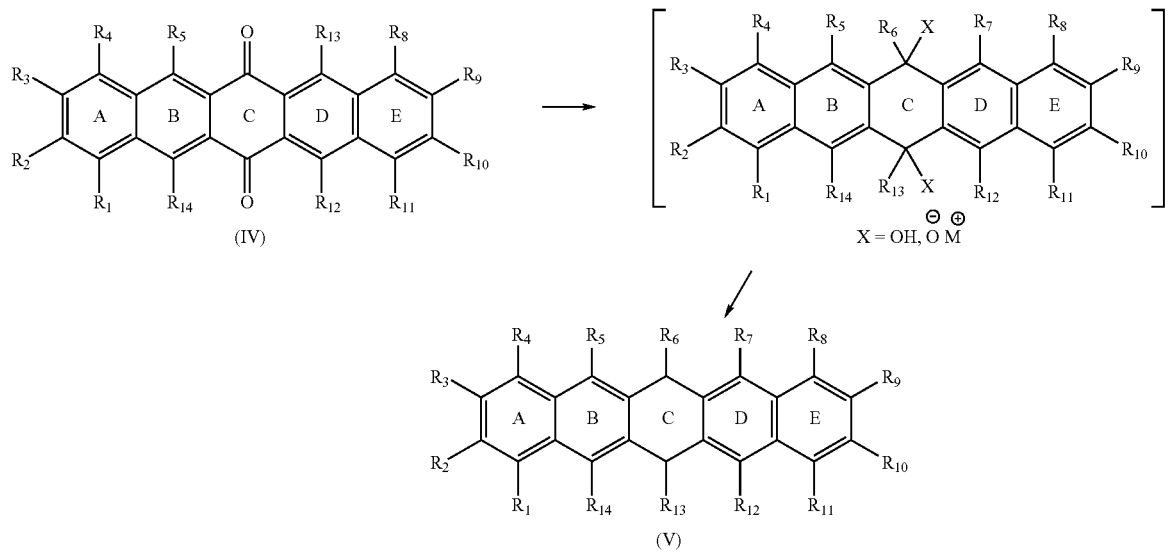

The methods of the present invention are specifically designed, at least in selected embodiments, for the production of pentacene compounds with substitutions in the 2 and 9 or 10 positions and the 6 and/or 13 positions if desired to generate tetra-substituted pentacenes. Such pentacene compounds are particularly suited for use in electronic applications by virtue of their desirable crystal packing properties Pentacenes normally pack in a 'herring bone' pattern which allows them to function as semiconductors. However, this precludes the attainment of the superior linear face to face geometry from a parallel array for electronic applications. The packing features of the molecules disclosed herein are unique. The inventors believe, to the best of their knowledge, the substituted pentacenes they have designed and synthesized are the first close packed molecules with this favourable motif. The X-ray analysis for the best compound(s) confirms their geometric juxtaposition. The three overlapping pentacenes, per unit cell, are p-p stacked in parallel with a separation of 3.5 Å, (the theoretical limit) with the pentacene rings offset from each other by 2.5 ring diameters. For this reason, the diene compounds of formula (IIa) or (IIb) optionally comprise substituents at $R_{26}$ or $R_{27}$, each comprising A-B, wherein A is a protective group, and B is a group to be protected. In this way, the methods of the invention may generate compounds of the formula III and formula IV.

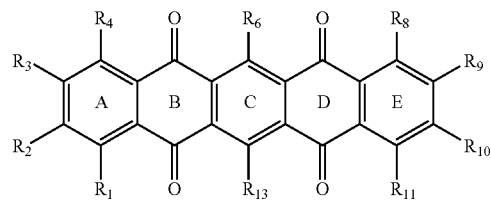

(III)

-continued

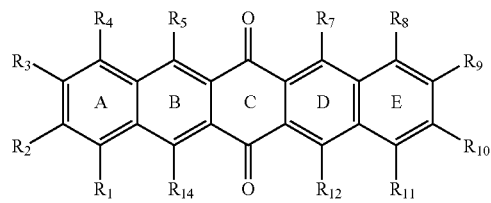

(IV)

wherein $R_1$ to $R_{14}$ are each independently unsubstituted or substituted, wherein optionally at least $R_2$ and $R_9$ or $R_{10}$ are substituted with A-B, or an alternative substituent. In this case, the substituents at $R_2$ and at $R_9$ or $R_{10}$ may be derived from $R_{26}$ or $R_{27}$ of the diene substrates.

Moreover, optional reduction of the compound of formula III and IV can lead to the production of pentacene compounds of formula V:

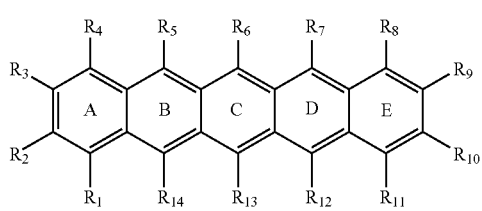

(V)

wherein optionally, $R_1$ to $R_{14}$ are each independently unsubstituted or substituted, are each independently selected from the group consisting of hydrogen, alkyl, alkenyl, alkynyl, aryl, a heterocycle, an electron-withdrawing group, a conjugated electron-withdrawing group, dicyanomethyl, halo, trifluoromethylsulfonyl, alkoxy, aryloxy, amine, haloalkyl, trialkylsilyl, trialkylsilylalkynyl, a thienyl group and a perfluorothienyl group that is unsubstituted or substituted with an alkyl, perfluoroalkyl, alkenyl, alkynyl, halo, haloalkyl, trialkylsilyl, trialkylsilylalkynyl, or a combination thereof, and wherein more optionally at least $R_2$ and $R_9$ or $R_{10}$ are substituted with A-B, or an alternative substituent. The substituents at the $R_2$ and $R_9$ or $R_{10}$ positions are optionally selected from acetylene, alkyl, aryl, heteroaryl, thienyl, perfluorothienyl, perfluorothienyl, alkylthienyl, perfluoroalkylthienyl, alkenyl, and alkynyl. Optionally, $R_2$ and $R_9$ or $R_{10}$ may comprise acetylene or a linker comprising one or more triple bonds, optionally substituted by halogen. Optionally, each A-B is a silica-based protective group. For example, each A may comprise a silyl ether such as TMS, TES, TBS, and TIPS, and each B may be acetylene or a heterocycle.

In another selected embodiment, the method of the present invention may comprise step (i) as recited above, thereby to generate an oligomeric compound comprising pentacyclic units linked by acetylene groups at the 2 and 9 or 10 positions. Without wishing to be bound by theory, it is considered possible that such oligomeric chains of core structures (each core structure comprising a linear array of five fused carbon rings) may exhibit very desirable crystal packing and electronic properties by virtue of optimal ∈-orbital electron overlap. The present invention therefore encompasses oligomeric or polymeric forms of the compounds disclosed herein.

In selected embodiments, the methods of the present invention are for the preparation of pentacenes at least comprising substitutions at the 2, and the 9 or 10 positions, and if desired 6 and/or 13 positions to generate tetra-substituted pentacenes, the method comprising the steps of:

(a) performing a stepwise or double Diels-Alder reaction by reacting a compound of formula IIa or IIb:

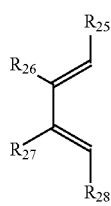

(IIa)

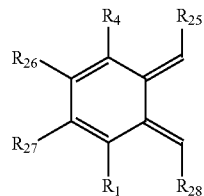

(IIb)

wherein A is a protective group, B is a group to be protected, wherein each R group is independently selected from the group consisting of hydrogen, an electron-withdrawing group, halo, a trialkylsilyl, trialkylsilylalkynyl, an alkoxy, an aryloxy, or an amine with a compound of formula IIa or a compound of formula IIb:

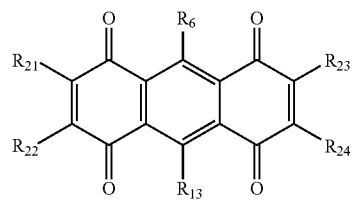

(Ia)

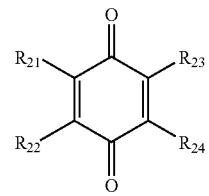

(Ib)

wherein each R group is independently selected from the group consisting of hydrogen, an electron-withdrawing group, halo, a trialkylsilyl, trialkylsilylalkynyl, an alkoxy, an aryloxy, or an amine, to form a mixture of compounds of formula IIIa and IIIb or a mixture of compounds of formula IVa and IVb:

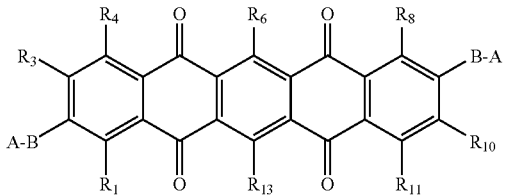

(IIIa)

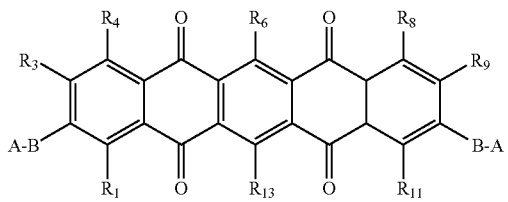

(IIIb)

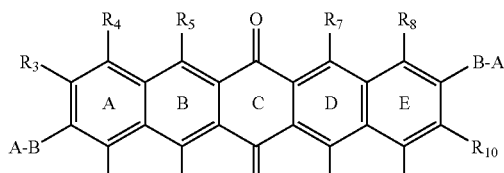
(IVa)

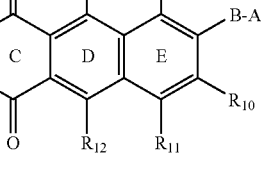
(IVb)

wherein A is a protective group, B is a group to be protected, and each R group is independently selected from the group consisting of hydrogen, alkyl, alkenyl, alkynyl, aryl, a heterocycle, an electron-withdrawing group, a conjugated electron-withdrawing group, dicyanomethyl, halo, trifluoromethylsulfonyl, alkoxy, aryloxy, amine, haloalkyl, trialkylsilyl, trialkylsilylalkynyl, and a thienyl group or a perfluorothienyl group that is unsubstituted or substituted with an alkyl, perfluoroalkyl, alkenyl, alkynyl, halo, haloalkyl, trialkylsilyl, trialkylsilylalkynyl, or a combination thereof.

(b) optionally separating the compounds of formula IIIa and 111b or the compounds of formula IVa and IVb, and selecting the compound of formula IIIa or formula IIIB or the compound of formula IVa or formula IVb for further processing;

(c) replacing each A or each A-B with a substituent elected from acetylene, alkyl, aryl, heteroaryl, alkyl, perfluoroalkyl, thienyl, perfluorothienyl, perfluoroalkenyl, alkenyl, and alkynyl with or without a linker comprising one or more triple bonds to form a 2,9- and/or a 2,10-disubstituted diquinone or quinone;

(d) subjecting the 2,9- and/or the 2,10-disubstituted diquinone or quinone to reducing/condensation/aromatization conditions to generate a pentacene substituted at least in the 2 position, and the 9 or 10 position and if desired 6 and/or 13 positions to generate tetra-substituted pentacenes.

The step of optional separation of the isomers III and IV may involve, for example, high performance liquid chromatography, fractional crystallization, or other suitable techniques that are well known in the art.

It should be noted that the diene may optionally include a protective group that will ultimately confer functionalization to the A and/or E ring of the pentacene. Any protective group may be used for this purpose in accordance with the corresponding protected group, and the protective group may be substituted as desired at a later stage. Particularly preferred protective groups include silyl ethers, which may be selected from, but not limited to, TMS, TES, TBS, or TIPS. Such protective groups can be substituted by methods known in the art. For example, diquinone or quinone compounds having only silyl ether substituents at the 2, and the 9 or 10 positions (originating from $R_{27}$ of the diene) may be subjected to desilylation and triflation to generate the compounds shown in formulae (IIIaa/IIIbb) and (IVaa/IVbb):

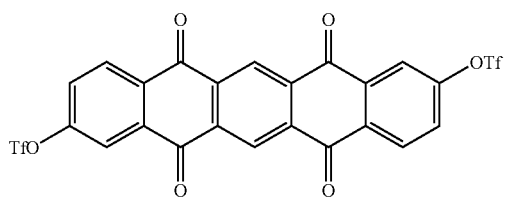
(IIIaa)

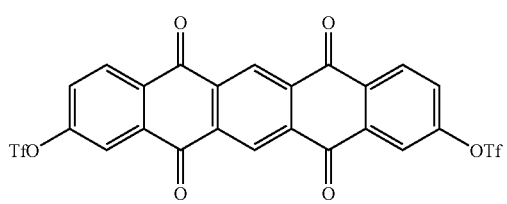
(IIIbb)

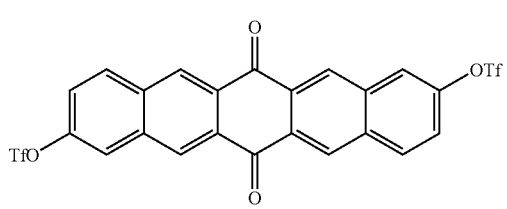
(IVaa)

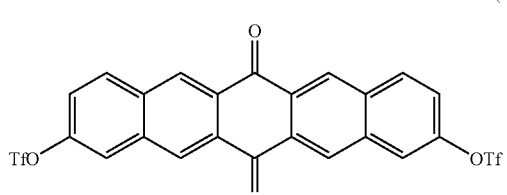
(IVbb)

Further processing of the compounds of formula IV can be carried out, for example by coupling reactions, such as for example a Sonogashira reaction involving Palladium coupling. Subsequent reduction of the diquinone or quinone core can generate the corresponding disubstituted pentacenes. If desired, the carbonyl groups in the core can be functionalized to generate tetrasubstituted pentacenes.

The methods of the present invention have proven highly successful and flexible in the production of 2,9- and 2,10-disubstituted pentacene compounds and 2,6,9,13- and/or 2,6,10,13-tetrasubstituted pentacene compounds. Importantly, the methods of the present invention present opportunities for the production of novel 2,9- or 2,10-disubstituted pentacenes comprising acetylene substituents, which are themselves very useful as intermediates for the generation of alternative substitutions or for coupling reactions.

The present invention further encompasses a wide range of compounds that at least comprise a linear series of five fused carbon rings.

Such compounds include those of the formula III and IV:

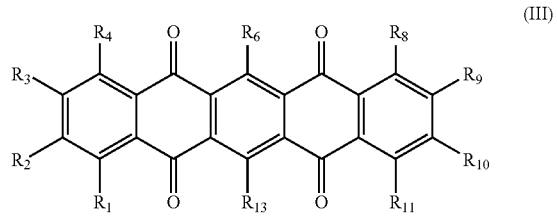
(III)

-continued

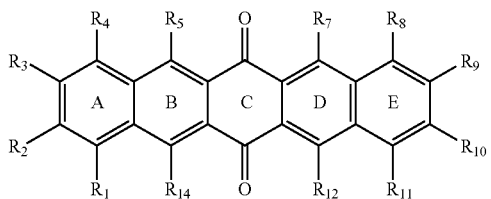

(IV)

wherein $R_1$ to $R_{14}$ group are each independently selected from the group consisting of hydrogen, alkyl, alkenyl, alkynyl, aryl, a heterocycle, an electron-withdrawing group, halo, trifluoromethylsulfonyl, alkoxy, aryloxy, amine, haloalkyl, trialkylsilyl, trialkylsilylalkynyl, and thienyl or perfluorothienyl group that is unsubstituted or substituted with an alkyl, perfluoroalkyl, alkenyl, alkynyl, halo, haloalkyl, trialkylsilyl, trialkylsilylalkynyl, or a combination thereof, wherein these steps may be performed in any order.

In selected embodiments, the present invention provides for a compound of formula V:

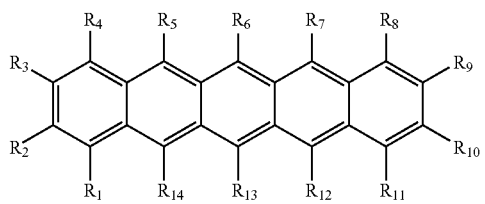

(V)

wherein $R_1$ to $R_{14}$ group are each independently selected from the group consisting of hydrogen, alkyl, alkenyl, alkynyl, aryl, a heterocycle, an electron-withdrawing group, a conjugated electron-withdrawing group, dicyanomethyl, halo, trifluoromethylsulfonyl, alkoxy, aryloxy, amine, haloalkyl, trialkylsilyl, trialkylsilylalkynyl, and a or thienyl or perfluorothienyl group that is unsubstituted or substituted with an alkyl, perfluoroalkyl, alkenyl, alkynyl, halo, haloalkyl, trialkylsilyl, trialkylsilylalkynyl, or a combination thereof; wherein these steps may be performed in any order.

Optionally, the compounds of formula III or IV include the proviso that the compounds of formula III or IV exclude pentacenes comprising only alkyl groups at $R_2$ and $R_9$ and/or $R_{10}$.

Optionally, the compounds of formula V include the proviso that when at least one of $R_1$, $R_2$, $R_3$, $R_4$, $R_8$, $R_9$, $R_{10}$, and $R_{11}$ are substituted with an electron-donating substituent, or a halogen, then the compound must include at least one further substituent at $R_5$, $R_6$, $R_7$, $R_{12}$, $R_{13}$, or $R_{14}$, wherein each R group is independently selected from the group consisting of hydrogen, alkyl, alkenyl, alkynyl, aryl, a heterocycle, an electron-withdrawing group, a conjugated electron-withdrawing group, dicyanomethyl, halo, trifluoromethylsulfonyl, alkoxy, aryloxy, amine, haloalkyl, trialkylsilyl, trialkylsilylalkynyl, and a thienyl or perfluorothienyl group that is unsubstituted or substituted with an alkyl, perfluoroalkyl, alkenyl, alkynyl, halo, haloalkyl, trialkylsilyl, trialkylsilylalkynyl, or a combination thereof; wherein these steps may be performed in any order.

Optionally, the compounds of formula III or IV comprise at least one substituent on each of the A and E rings of the core structure. More optionally, the compound comprises at least one substituent on each of the A and E rings, and at least one substituent on at least one of the B, C, or D rings of the core structure. More optionally, the compound comprises substituents at least at the 2, and the 9 or 10 positions plus the 6 and 13 positions if desired. Optionally, the substituents at the 2, and the 9 or 10 positions are acetylene groups, or alkyl groups or thienyl groups or perfluorothienyl groups or are each attached to the core structure via a linker comprising one or more triple bonds. Optionally, in accordance with the compound of formula III or formula IV each substituent is independently selected from hydroxyl, alkyl, alkoxy, alkenyl, alkynyl, aryl, heteroaryl, alkylthienyl, perfluoroalkyl, thienyl, acetylene, halogen, and triflate. More optionally, each substituent is substituted by alkynyl, or thienyl or perfluorothienyl or trialkylsilylalkynyl or halogen.

Without wishing to be bound by theory, the methods of the invention provide for rapid synthesis of the compounds of the invention. Importantly, the methods afford a significant degree of flexibility with regard to the substituents located on the substrates during synthesis of the five fused carbon ring core structure. Moreover, the possibility of using different dienes to generate pentacene compounds presents a further opportunity to manipulate the substituents on the core structure. The optional reduction and/or related reactions of the anthradiquinone and quinone compounds of the invention presents further opportunities for substituent addition or replacement.

The pentacene compounds of the present invention are differentiated over those of the prior art by virtue of the wide range of possible substituents that can be positioned on the A and E rings, as well as the B, C, and D rings. In one particularly advantageous embodiment, the A and E rings may comprise acetylene substituents, or may comprise substituents attached to the core structure via a linker of one or more triple bonds. This option presents unique opportunities for the provision of a wide range of substituents at such positions on the core structure, for example by manipulation or replacement of the acetylene and by manipulation or replacement of the carbonyl groups. These groups include independently selected from the group consisting of hydrogen, alkyl, alkenyl, alkynyl, aryl, a heterocycle, an electron-withdrawing group, a conjugated electron-withdrawing group, dicyanomethyl, halo, trifluoromethylsulfonyl, alkoxy, aryloxy, amine, haloalkyl, trialkylsilyl, trialkylsilylalkynyl, and a thienyl or or perfluorothienyl group that is unsubstituted or substituted with an alkyl, perfluoroalkyl, alkenyl, alkynyl, halo, haloalkyl, trialkylsilyl, trialkylsilylalkynyl, or a combination thereof.

Generation of Organic Thin Film Transistors (OTFTs) or Other Electronic Components The present invention provides methods for the production of compounds suitable for use in the manufacture of components, specifically organic semiconductors of p-type and/or n-type components, of Organic Thin Film Transistors and other electronic devices. The present invention encompasses such components, their manufacture, and OTFTs containing them. The methods of the present invention may be useful in the production of any types of OTFTs that incorporate pentacene derivative molecules.

Typically, a thin film transistor includes a gate electrode, a gate dielectric on the gate electrode, a source electrode and a drain electrode adjacent to the gate dielectric, and a semiconductor layer adjacent to the gate dielectric and adjacent to the source and drain electrodes. More specifically, an organic thin film transistor (OTFT) has an organic semiconductor layer. Such OTFTs are known in the art as shown, for example, in U.S. Pat. No. 6,433,359, issued Aug. 13, 2002, and U.S. Pat. No. 6,617,609 issued Sep. 9, 2003, which are herein incorporated by reference.

A substrate can be used to support the OTFT, e.g., during manufacturing, testing, storage, use, or any combination thereof. The gate electrode and/or gate dielectric may provide sufficient support for the intended use of the resultant OTFT and another substrate is not required. For example, doped silicon can function as the gate electrode and support the OTFT. In another example, one substrate may be selected for testing or screening various embodiments while another substrate is selected for commercial embodiments. In another embodiment, a support may be detachably adhered or mechanically affixed to a substrate, such as when the support is desired for a temporary purpose. For example, a flexible oligomeric substrate may be adhered to a rigid glass support, which support could be removed. In some embodiments, the substrate does not provide any necessary electrical function for the OTFT. This type of substrate is termed a "non-participating substrate" in this document.

Useful substrate materials can include organic and/or inorganic materials. For example, the substrate may comprise inorganic glasses, ceramic foils, polymeric materials, filled polymeric materials, coated metallic foils, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbomenes, polyphenyleneoxides, poly(ethylene naphthalenedicarboxylate) (PEN), poly(ethylene terephthalate) (PET), poly(phenylene sulfide) (PPS), and fiber-reinforced plastics (FRP).

The gate electrode can be any useful conductive material. For example, the gate electrode may comprise doped silicon, or a metal, such as aluminum, chromium, copper, gold, silver, nickel, palladium, platinum, tantalum, and titanium. Conductive polymers also can be used, for example polyaniline, poly(3,4-ethylenedioxythiophene)/poly(styrene sulfonate) (PEDOT:PSS). In addition, alloys, combinations, and multilayers of these materials may be useful.

The gate dielectric is provided on the gate electrode, for example, through a deposition method. This gate dielectric electrically insulates the gate electrode under the operating conditions of the OTFT device from the balance of the device. Thus, the gate dielectric comprises an electrically insulating material. The gate dielectric should have a dielectric constant above about 2, more optionally above about 5. The dielectric constant of the gate dielectric also can be very high, for example, 80 to 100 or even higher. Useful materials for the gate dielectric may comprise, for example, an organic or inorganic electrically insulating material, or combinations thereof.

The gate dielectric may comprise a polymeric material, such as polyvinylidenefluoride (PVDF), cyanocelluloses, polyimides, epoxies, etc. In some embodiments, an inorganic capping layer comprises the outer layer of an otherwise polymeric gate dielectric for improved bonding to the polymeric layer and/or improved dielectric properties.

Specific examples of inorganic materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these can be used for the gate dielectric. Of these materials, aluminum oxides, silicon oxides, silicon nitrides, and zinc selenide are preferred.

The gate dielectric can be deposited in the OTFT as a separate layer, or formed on the gate such as by oxidizing, including anodizing, the gate material to form the gate dielectric.

The source electrode and drain electrode are separated from the gate electrode by the gate dielectric, while the organic semiconductor layer can be over or under the source electrode and drain electrode. The source and drain electrodes can be any useful conductive material. Useful materials include those materials described above for the gate electrode, for example, aluminum, barium, calcium, chromium, copper, gold, silver, nickel, palladium, platinum, titanium, polyaniline, PEDOT:PSS, other conducting polymers, alloys thereof, combinations thereof, and multilayers thereof.

The thin film electrodes (e.g., gate electrode, source electrode, and drain electrode) can be provided by any useful means such as physical vapor deposition (e.g., thermal evaporation, sputtering), plating, or ink jet printing. The patterning of these electrodes can be accomplished by known methods such as shadow masking, additive photolithography, subtractive photolithography, printing, transfer printing, microcontact printing, and pattern coating.

The organic semiconductor layer, produced in accordance with the present invention, can be provided by any useful means, such as for example, vapor deposition, solution deposition, spin coating, and printing techniques, all of which are well known in the art.

Importantly, the compounds of the present invention can be used in the manufacture of a wide range of electronic devices and semiconductor components, including but not limited to, Organic Thin Film Semiconductor (OTFS), an Organic Field-Effect Transistor (OFET), an Organic Light Emitting Diode (OLED), a solar cell, and a device for solar energy conversion.

EXAMPLES

Scheme 5: Route from 1,4,5,8-anthradiquinone to disubtituted pentacene

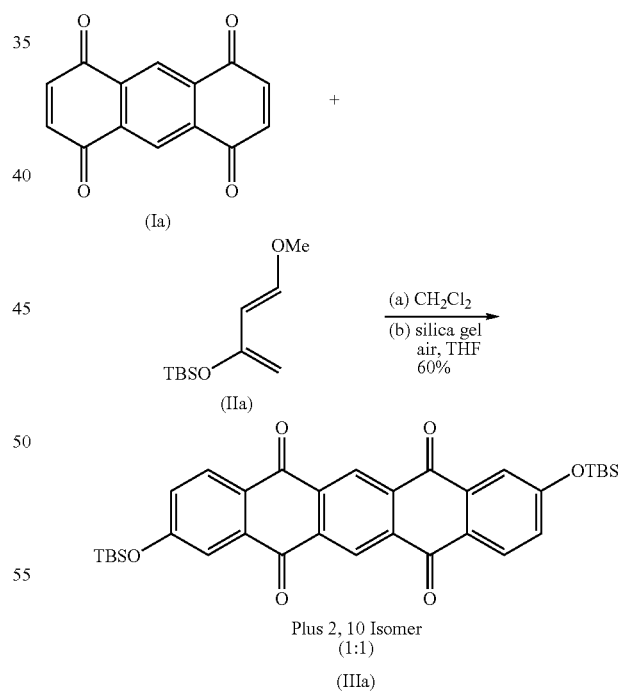

Example 1

Cycloaddition with 1,4,5,8-anthradiquinone 2,9/2,10-Bis(t-butyldimethylsiloxy)-5,7,12,14-pentacene-diquinone: 1,4,5,8-Anthradiquinone (2.45 g, 10.3 mmol, 1 eq) and trans-3-(t-butyldimethylsilyoxy)-1-methoxy-1,3-butadiene (5.14 mL, 21.6 mmol, 2.1 eq) were combined in $CH_2Cl_2$ and stirred at room temperature (22° C.) for 20 h. The reaction was concentrated, taken up in THF, silica gel was added, and the suspension was stirred open to air for 24 h. The reaction was filtered through a silica gel plug with $CH_2Cl_2$ to afford the adducts. The plug was flushed with THF to recover the unaromatized material. Silica gel was added to the THF fraction and this slurry was stirred open to air for 24 h. Filtration through a silica gel plug with $CH_2Cl_2$ afforded additional product. The silica gel oxidation/filtration was repeated until all of the unaromatized material was converted to the products. The diquinones were isolated as a yellow solid (3.72 g, 60%, 1:1 mixture). The isomers could be separated by preparative HPLC ($CH_2CL_2$/hexane 70:30) or preferably by fractional crystallization from chloroform.

126.5 (d), 117.7 (d), 25.5 (q), 18.3 (s), −4.3 (q); MS (EI) m/z 541.2 ($M^+$-t-Bu, 100), 485.1 (8), 242.0 (19), 162.0 (34); IR $CDCl_3$) v 2957.6, 2930.7, 1677.7, 1591.9 $cm^{-t}$; HRMS calcd for $C_{30}H_{29}O_6Si_2$ 541.1502 ($M^+$-t-Bu), found 541.1510.

2,10-Bis(t-butyldimethylsiloxy)-5,7,12,14-pentacene-diquinone: mp: >270° C.; $^1$H NMR (500 MHz, $CDCl_3$) δ 9.18 (s, 1H), 9.14 (s, 1H), 8.28 (d, J=8.6 Hz, 2H), 7.71 (d, J=2.4 Hz, 2H), 7.24 (dd, J=8.2, 2.6 Hz, 2H), 1.01 (s, 18H), 0.30 (s, 12H); $^{13}$C NMR (125 MHz, $CDCl_3$) δ 181.8 (s), 180.7 (s), 161.9 (s), 137.0 (s), 136.6 (s), 135.6 (s), 130.4 (d), 127.5 (s), 127.1 (d), 127.0 (d), 126.5 (d), 117.7 (d), 25.5 (q), 18.3 (s), −4.3 (q); IR ($CDCl_3$) v 2955.8, 2927.2, 1675.0, 1590.9 $cm^{-1}$; MS (EI) m/z 541.2 ($M^+$-t-Bu, 15), 504.9 (3), 162.0 (18), 57.1 (100); HRMS calcd for $C_{30}H_{29}O_6Si_2$ 541.1502 ($M^+$-t-Bu), found 541.1516.

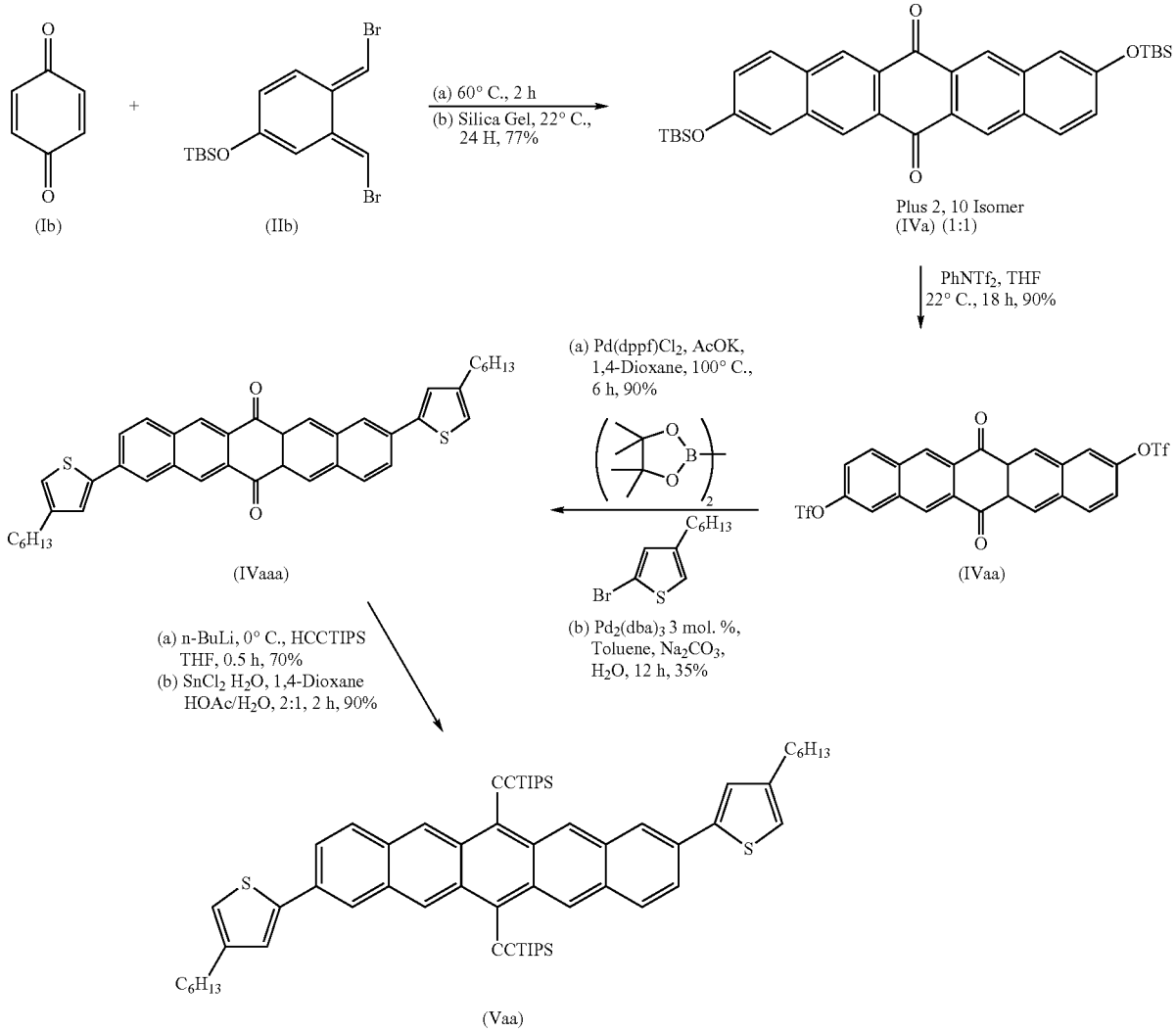

Scheme 6: Route from quinone to a tetrasubstituted pentacene 2,9-Bis(t-butyldimethylsiloxy)-5,7,12,14-pentacene-diquinone: mp: >270° C.; $^1$H NMR (500 MHz, $CDCl_3$) δ 9.15 (s, 2H), 8.28 (d, J=8.6 Hz, 2H), 7.70 (d, J=2.5 Hz, 2H), 7.24 (dd, J=8.5, 2.6 Hz, 2H), 1.01 (s, 18H), 0.30 (s, 12H); $^{13}$C NMR (125 MHz, $CDCl_3$) δ 181.8 (s), 180.7 (s), 161.9 (s), 136.9 (s), 136.7 (s), 135.6 (s), 130.4 (d), 127.5 (s), 127.0 (d), Example 2

Cycloaddition with Quinone 2,9/2,10-Bis(t-butyldimethylsiloxy)-6,13-pentacene-quinone: (3,4-Bis(dibromomethyl)phenoxy)(tert-butyl)dimethylsilane (1.10 g, 2 mmol) and benzoquinone (218 mg, 2 mmol) were added to the stirred ionic liquid (1-butyl-3-methylimidazolim iodide) (5 g). The mixture was heated to 60° C. and stirred for a further 2 hours. The mixture was washed four times with ether, and the ether layers combined. The ether solution was concentrated under reduced pressure and the solid washed with acetone to afford a mixture (1:1) of the adducts (436 mg, 77%) as a yellow solid. The remaining ionic liquid phase was dried under vacuum and directly reused in the subsequent experiments. Fractional recrystallization from $CH_2Cl_2$ gave the pure adducts.

2,9-Bis(t-butyldimethylsiloxy)-6,13-pentacenequinone: Yellow needles. mp: <270° C. $^1$H NMR (300 MHz, $CDCl_3$) δ 8.83 (s, 2H), 8.73 (s, 2H), 7.98 (d, J=9 Hz, 2H), 7.41 (d, J=2.1 Hz, 2H), 7.27 (m, 2H), 1.02, (s, 18H), 0.29 (s, 12H); $^{13}$C NMR (75 MHz, $CDCl_3$) δ 183.5, 157.1, 137.4, 132.2, 131.4, 131.2, 130.0, 129.3, 128.4, 126.2, 116.9, 26.0, 18.7, −3.9; IR ($CH_2Cl_2$) ν 3055, 3005, 1712 $cm^{-1}$; MS (EI) m/z 568 ($M^+$) (63), 545 (4.6), 511 (100), 455 (14), 227 (28); HRMS calculated for ($M^+$) 568.24651, found 568.24548.

2,10-Bis(t-butyldimethylsiloxy)-6,13-pentacenequinone: Yellow powder mp: >270° C.; $^1$H NMR (300 MHz, $CDCl_3$) δ 8.82 (s, 2H), 8.73 (s, 2H), 7.99 (d, J=9 Hz, 2H), 7.42 (d, J=2.1 Hz, 2H), 7.27 (m, 2H), 1.06 (s, 18H), 0.33 (s, 12H); $^{13}$C NMR (75 MHz, $CDCl_3$) δ 183.8, 183.1, 157.1, 137.3, 132.2, 131.3, 131.2, 129.9, 129.4, 128.5, 126.3, 117.0, 26.1, 18.8, −3.8; IR (thin-film) ν 2955, 2857, 1672, 1619, 829 $cm^{-1}$; MS (EI) m/z 568 ($M^+$) (54), 511 (100), 227 (28), 143 (12); HRMS calculated for ($M^+$) 568.24651, found 568.24910.

Example 3

Conversion of the Quinone to the Triflate 2,9-Bis(trifluoromethylsulfonyloxy)-6,13-pentacenequinone: 2,9-Bis-(tertbutyl-dimethylsilanyloxy)-pentacene-6-13-dione (288 mg, 0.5 mmol) was dissolved in THF (150 mL), cooled to 0° C. and TBAF (1.1 mL, 1.1 mmol, 1M in THF) added. After 15 min., $Tf_2NPh$ (500 mg, 1.4 mmol) in THF (10 mL) was cannulated into the reaction flask and warmed to 22° C. After 18 h, the reaction was concentrated to 50 mL, diluted with ether, washed with 1 M HCl, 5% $NaHCO_3$, and $H_2O$. The ether solution was concentrated to 30 mL and filtered through a sintered glass funnel to obtain the bis-triflate as a pale yellow solid (278 mg, 90%) that was used directly without further purification for the next step.

Example 4

Conversion of the Triflate to the Thienyldione 2,9-Bis(4,4,5,5-tetramethyl-1,3,2-dioxaboron-2-yl)pentacene-6,13-dione (or bis(pinacolato)diboronylpentacene-6,13-dione): Potassium acetate (590 mg, 6 mmol) was flame dried in a flask under high vacuum. The flask was cooled to 22° C., the di-triflate (604 mg, 1 mmol), $PdCl_2$(dppf), $CH_2Cl_2$ (24 mg, 0.03 mmol), bis(pinacolato)diboron (635 mg, 2.5 mmol) and 1,4-dioxane (10 mL) were sequentially added. The mixture was refluxed for 6 h. Cooled and the mixture filtered through Celite®. The brown solution was concentrated, washed with $Et_2O$/petroleum ether (1:4) to remove residual contaminants. The solid was then dried under vacuum to give the bis-boronylquinone (500 mg, 90%).

$^1$H NMR ($CDCl_3$, 500 MHz) δ 8.97 (s, 2H), 8.90 (s, 2H), 8.60 (s, 2H), 8.08 (d, J=8.3 Hz, 2H), 8.03 (d, J=8.3 Hz, 2H), 1.40 (s, 24H). $^{13}$C NMR ($CDCl_3$, 100 MHz) δ 182.9, 138.1, 136.7, 134.6, 134.0, 131.3, 130.6, 130.6, 129.5, 129.1, 84.4, 25.0; HRMS (EI) calculated for ($M^+$) 560.2541, found 560.2538.

2,9-Bis(4-hexylthienyl)pentacene-6,13-dione: The bis-boronylquinone (200 mg, 0.36 mmol), $Pd_2$(dba)$_3$ (9.7 mg, 0.12 mmol, 0.03 equiv.), $Na_2CO_3$ (114 mg, 0.06 equiv.), 2-bromo-4-hexylthiophene (220 mg ca. 178 μL, 0.9 mmol, 2.5 equiv.), toluene (2 ml) and water (0.5 mL) were introduced sequentially to an argon purged flame dried flask. The reaction (Ag atmosphere) was refluxed for 12 h, cooled, $CH_2Cl_2$ (25 mL), added, followed by $Na_2SO_4$ (~2 g) and mixture stirred vigorously for 5 min. The mixture was filtered through Celite® and concentrated. Flash chromatography (silica), initial elution with $Et_2O$ followed by hot $CHCl_3$ afforded the bis-thienylquinone (80 mg, 35%).

$^1$H NMR ($CDCl_3$, 500 MHz) δ (ppm) 8.71 (s, 4H), 8.09 (s, 2H), 7.95 (d, J=8.7 Hz, 2H), 7.78 (d, J=8.7 Hz, 2H), 7.28 (s, 2H), 6.93 (s, 2H), 2.60 (t, J=7.5 Hz, 4H), 1.64 (m, 4H), (m, 12H), (t, J=6.7 Hz, 6H); $^{13}$C NMR ($CDCl_3$, 75 MHz, 318K) δ 144.8, 142.5, 135.5, 134.1, 131.0, 130.6, 130.2, 129.5, 129.4, 127.5, 126.1, 125.1, 121.3, 31.7, 30.6, 30.4, 29.0, 22.6, 14.1; HRMS (EI) calculated for ($M^+$) 640.2470, found 640.2512

Example 5

Conversion of the thienyldione to the thienyl(triisopropylsilylethynyl)pentacene 2,9-Bis(4-hexylthienyl)pentacene-6,13-dihydroxy-6,13-bis(triisopropylsilylethynyl)dione: Triisopropylsilylacetylene (0.2 mL, 0.47 mmol) was added dropwise to a solution of n-BuLi (2.5 M, hexanes, 19 ml, 0.47 mmol) maintained at 0° C. The reaction was warmed to 22° C. and stirred for 1 h. This solution was transferred via syringe to a THF (5 mL) suspension of 2,9-bis(4-hexylthienyl)pentacene-6,13-dione (50 mg, 0.078 mmol) maintained at 0° C. The reaction was warmed to 22° C. and stirred for further 12 h. The reaction was quenched with $NH_4Cl$ (sat. aq.), extracted with ether, washed, with water and brine. Dried ($Na_2SO_4$), filtered, concentrated, and chromatographed (flash), (petroleum ether/AcOEt, 95:5) to afford 2,9-bis(4-hexylthienyl)pentacene-6,13-dihydroxy-6,13-bis(triisopropylsilylethynyl)dione (54 mg, 70%).

$^1$H NMR (500 MHz, $CDCl_3$) δ 8.66 (d, J=3.9 Hz, 2H), 8.62 (d, 3.9 Hz, 2H), 8.08 (d, J=5.9 Hz, 2H), 7.88 (dd, J=9.0 Hz, J=5.9 Hz), 7.77 (dd, J=9.0 Hz, J=1.5 Hz), 7.28 (s, 2H), 6.92 (s, 2H), 3.39 (s, 2H), 2.64 (t, J=, 4H), 1.66 (m, 4H), 1.31 (m, 12H), 1.08 (m, 42H), 0.89 (t, J=6.7 Hz, 6H); $^{13}$C NMR (125 MHz, $CDCl_3$) δ 144.5, 143.7, 136.9, 136.2, 133.4, 133.0, 132.3, 128.7, 126.0, 125.8, 125.2, 125.1, 124.0, 120.0, 109.2, 89.7, 69.6, 31.7, 30.6, 30.4, 29.0, 22.6, 18.6, 14.1, 11.2.

2,9-Bis(4-hexylthienyl)-6,13-bis(triisopropylsilylethynyl) pentacene: $SnCl_2$.2$H_2O$ (226 mg, 1 mmol) was added to a 1,4-dioxane (2 mL)/AcOH (1 mL) solution of 2,9-bis(4-hexylthienyl)pentacene-6,13-dihydroxy-6,13-bis(triisopropylsilylethynyl)dione (100 mg, 0.1 mmol) was dissolved in a solution and added $SnCl_2$.2$H_2O$ (226 mg, 1 mmol, at 22° C. The resulting deep green solution was stirred for 1 h. The reaction was diluted with $Et_2O$, washed with $H_2O$ (3×) brine, dried ($Na_2SO_4$), filtered, and concentrated. Chromatography ((flash silica) $CH_2Cl_2$/petroleum ether; 1:1) to afford 2,9-bis (4-hexylthienyl)-6,13-bis(triisopropylsilylethynyl)pentacene (90 mg, 90%), a green blue solid.

$^1$H NMR: (300 MHz, $CDCl_3$): 9.26 (s, 4H), 8.13 (s, 2H), 7.99 (d, J=8.9 Hz, 2H), 7.71 (d, J=9.4 Hz, 2H), 7.38 (s, 2H), 6.99 (s, 2H), 2.70 (t, J=7.6 HZ, 4H), 1.76-1.66 (m, 4H), 1.42 (s, 42), 1.49-1.36 (m, 12), 0.97-0.91 (m, 6H); $^{13}$C NMR: (75

MHz, CDCl$_3$): 144.5, 143.7, 132.1, 131.7, 131.3, 130.9, 130.7, 129.1, 126.1, 126.0, 125.2, 125.1, 123.4, 120.1, 118.1, 107.1, 104.4, 31.6, 30.5, 30.3, 29.6, 28.9, 22.5, 18.9, 14.0, 11.5; IR (film): 2923, 2862, 2853, 2133, 1622, 1456, 1367.

While the invention has been described with reference to particular selected embodiments thereof, it will be apparent to those skilled in the art upon a reading and understanding of the foregoing that numerous methods for substituted pentacene production, other than the specific embodiments illustrated are attainable, which nonetheless lie within the spirit and scope of the present invention. It is intended to include all such designs, assemblies, assembly methods, and equivalents thereof within the scope of the appended claims. With particular reference to the synthetic methods of the present invention, each method as claimed is intended to encompass obvious chemical equivalents thereof.

The invention claimed is:

1. A method for the preparation of a compound comprising at least one linear series of five fused carbon rings, the method comprising the steps of:
   (a) providing a compound containing at least one quinone moiety;
   (b) providing an unsubstituted or substituted acyclic, cyclic or heterocyclic diene;
   (c) performing a double or stepwise cycloaddition reaction between the compound containing the quinone moiety and the diene to generate a carbonyl substituted core structure comprising five fused carbon rings sequentially identified as rings A, B, C, D, and E of general formula V, and optionally comprising additional substituents:

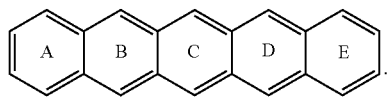

(V)

2. The method according to claim 1, wherein in step (a) the compound containing at least one quinone moiety has the general formula Ib:

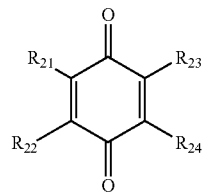

(Ib)

wherein each of R$_{21}$, R$_{22}$, R$_{23}$, and R$_{24}$ is independently selected from the group consisting of hydrogen, an electron-withdrawing group, halo, a trialkylsilyl, trialkylsilylalkynyl, an alkoxy, an aryloxy, and an amine.

3. The method according to claim 1, wherein in step (b) the diene compound has the general formula IIb:

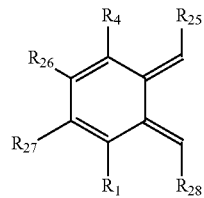

(IIb)

wherein each of, R$_4$, R$_{25}$, R$_{26}$, R$_{27}$, and R$_{28}$ is independently selected from the group consisting of hydrogen, an electron-withdrawing group, halo, a trialkylsilyl, trialkylsilylalkynyl, an alkoxy, an aryloxy, and an amine.

4. The method according to claim 1, wherein step (c) comprises a double Diels-Alder reaction between the quinone and two diene molecules.

5. A method for the preparation of a compound comprising at least one linear series of five fused carbon rings, the method comprising the steps of:
   (a) providing an unsubstituted or substituted quinone of the general formula Ib:

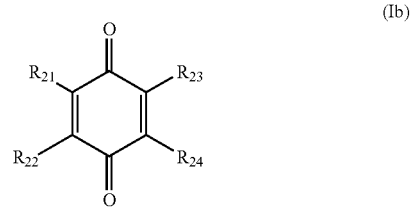

(Ib)

wherein each of R$_{21}$, R$_{22}$, R$_{23}$, and R$_{24}$ is independently selected from the group consisting of hydrogen, an electron-withdrawing group, halo, a trialkylsilyl, a trialkylsilylalkynyl, an alkoxy, an aryloxy, and an amine;
   (b) providing an unsubstituted or substituted acyclic diene of the general formula IIb:

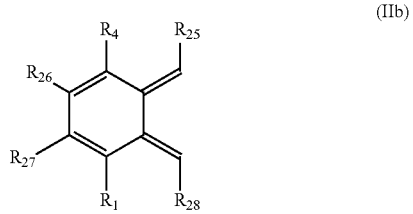

(IIb)

wherein each of R$_1$, R$_4$, R$_{25}$, R$_{26}$, R$_{27}$, and R$_{28}$ is independently selected from the group consisting of hydrogen, an electron-withdrawing group, halo, a trialkylsilyl, a trialkylsilylalkynyl, an alkoxy, an aryloxy, and an amine;
   (c) performing a double or stepwise cycloaddition reaction between the quinone and the diene to generate a core structure comprising five fused carbon rings sequentially identified as rings A, B, C, D, and E;
   (d) optionally replacing or adding selected substituents;
to generate a product of general formula IV, wherein each R group is independently selected from the group consisting of hydrogen, alkyl, alkenyl, alkynyl, aryl, a heterocycle, an electron-withdrawing group, halo, trifluoromethylsulfonyl, alkoxy, aryloxy, amine, haloalkyl, trialkylsilyl, trialkylsilylalkynyl, a thienyl group and a perfluorothienyl group that is unsubstituted or substituted with an alkyl, perfluoroalkyl, alkenyl, alkynyl, halo, haloalkyl, trialkylsilyl, trialkylsilylalkynyl, or a combination thereof:

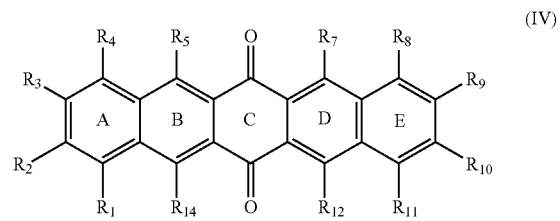

(IV)

wherein these steps may be performed in any order.

6. The method according to claim 5, wherein in step c) isomeric products are generated and the method further comprises the step of:

e) separating the isomeric products.

7. The method according to claim 5, further comprising the step of:

(e) subjecting the product to reduction and/or condensation and/or aromatization conditions to generate a corresponding unsubstituted or substituted pentacene.

8. The method according to claim 5, further comprising the step of:

(e) performing a coupling reaction to link two or more core structures.

9. A method according to claim 5, further comprising at least two steps selected from:

separating the isomeric products;

subjecting the product to reduction and/or condensation and/or aromatization conditions to generate a corresponding unsubstituted or substituted pentacene; or performing a coupling reaction to link two or more core structures;

wherein the steps may be performed in any order.

10. The method according to claim 5, wherein in the compound of formula IIb, one of $R_{26}$ or $R_{27}$ comprises A-B, wherein A is a protective group, and B is a group to be protected, and wherein in the compound of formula IV, $R_2$ and one of $R_9$ or $R_{10}$ are A-B.

11. The method according to claim 10, further comprising replacing each A-B at $R_2$, and one of $R_9$ or $R_{10}$ with an R group independently selected from the group consisting of hydrogen, alkyl, alkenyl, alkynyl, aryl, a heterocycle, an electron-withdrawing group, halo, trifluoromethylsulfonyl, alkoxy, aryloxy, amine, haloalkyl, trialkylsilyl, trialkylsilylalkynyl, a thienyl group and perfluorothienyl group that is unsubstituted or substituted with an alkyl, perfluoroalkyl, alkenyl, alkynyl, halo, haloalkyl, trialkylsilyl, trialkylsilylalkynyl, or a combination thereof.

12. The method according to claim 7, wherein the step of subjecting the product to reduction and/or condensation and/or aromatization conditions generates a pentacene compound of formula V:

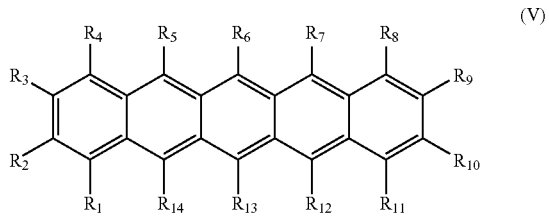

(V)

wherein $R_2$, and one of $R_9$ or $R_{10}$ are A-B, and each remaining R group is independently selected from the group consisting of hydrogen, alkyl, alkenyl, alkynyl, aryl, a heterocycle, an electron-withdrawing group, a conjugated electron-withdrawing group, dicyanomethyl, halo, trifluoromethylsulfonyl, alkoxy, aryloxy, amine, haloalkyl, trialkylsilyl, trialkylsilylalkynyl, a thienyl group and a perfluorothienyl that is unsubstituted or substituted with an alkyl, perfluoroalkyl, alkenyl, alkynyl, halo, haloalkyl, trialkylsilyl, trialkylsilylalkynyl, or a combination thereof.

13. The method according to claim 5, wherein $R_2$ and one of $R_9$ or $R_{10}$ comprise acetylene, thienyl, perfluorothienyl, alkylthienyl, perfluoroalkanylperfluorothienyl, heterocycle or a linker comprising one or more triple bonds, unsubstituted or substituted by halogen and/or triflate.

14. The method according to claim 13, wherein the method comprises the step or performing a coupling reaction to link two or more core structures thereby to generate an oligomeric compound comprising multiple units of said core structure linked by acetylene, heteroaryl, thienyl, perfluorothienyl, alkylthienyl, perfluoroalkylthienyl, perfluoroalkanylperfluorothienyl or heterocycle groups at least at the 2-position, and one of the 9 or 10 positions.

15. The method according to claim 10, wherein each A-B comprises $Si(R_{30}, R_{31}, R_{32})$ wherein each of $R_{30}, R_{31}, R_{32}$ is independently selected from the group consisting of hydrogen, an alkyl, alkenyl, alkynyl, aryl, TMS, TES, TBS, TIPS, diphenyl tertiary butyl, OSi, OH, OTf, OTs, OMs, ONs, NSi, acetylene, a thienyl, a perfluorothienyl, and a heterocycle.

16. The method according to claim 10, wherein each B is O, S, Se, or N.

17. The method according to claim 11, wherein in the step of replacing or adding substituents comprises replacing each A-B with Tf-O, halogen, or a substituent comprising a metal atom selected from Al, B, Cu, Co, Cr, Fe, Li, Mg, Ni, Pd, Pt, Si, Sn, Ti, and Zn.

18. The method according to claim 17, wherein the method further comprises replacing each substituent with an acetylene group, or a group comprising a linker comprising one or more triple bonds, a substituted aryl, a substituted thienyl, a perfluorothienyl, a alkylthienyl, a perfluoroalkylthienyl, a perfluoroalkanylperfluorothienyl or substituted heterocycle with substitutents selected from alkyl, alkenyl, and aryl.

19. A method for the preparation of a pentacene comprising substitutions at least at the 2 position, and at one of the 9 or 10 position, the method comprising the steps of:

(a) performing a stepwise or double Diels-Alder reaction or an equivalent reaction by reacting a compound of formula IIb:

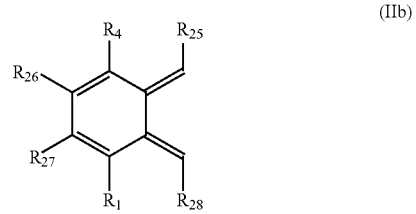

(IIb)

wherein one of $R_{26}$ or $R_{27}$ comprises A-B, A is a protective group, B is a group to be protected, and each R group is independently selected from the group consisting of hydrogen, an electron-withdrawing group, halo, a trialkylsilyl, trialkylsilylalkynyl, an alkoxy, an aryloxy, and an amine;

with a compound of formula Ib:

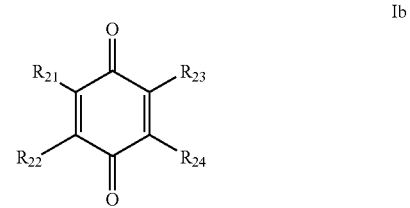

Ib wherein each of $R_{21}$, $R_{22}$, $R_{23}$, and $R_{24}$ is independently selected from the group consisting of hydrogen, an electron-withdrawing group, halo, a trialkylsilyl, a trialkylsilylalkynyl, an alkoxy, an aryloxy, and an amine;

(b) replacing or adding selected substituents wherein each R group is independently selected from a group consisting of hydrogen, an electron-withdrawing group, halo, a trialkylsilyl, a trialkylsilylalkynyl, an alkoxy, an aryloxy, and an amine; wherein the method generates compounds of formula IVa and/or formula IVb:

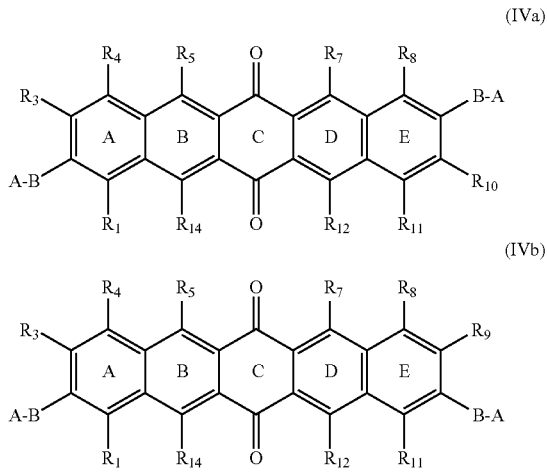

wherein A is a protective group, B is a group to be protected, and each R group is independently selected from the group consisting of hydrogen, alkyl, alkenyl, alkynyl, aryl, a heterocycle, an electron-withdrawing group, halo, trifluoromethylsulfonyl, alkoxy, aryloxy, amine, haloalkyl, trialkylsilyl, trialkylsilylalkynyl, a thienyl group and a perfluorothienyl group that is unsubstituted or that is substituted with an alkyl, perfluoroalkyl, perfluoroalkanylperfluorothienyl, alkenyl, alkynyl, halo, haloalkyl, trialkylsilyl, trialkylsilylalkynylthienyl, or a combination thereof; in which these steps may be performed in any order.

20. The method according to claim 19 further comprising at least one of the steps of:
(c) separating the compounds of formula (IVa) and formula (IVb), and selecting the compound of formula (IVb) and/or the compound of formula (IVa) for further processing;
(d) replacing each A or each A-B with an alternative substituent, with or without a linker comprising one or more triple bonds to form a 2,9- and/or a 2,10-disubstituted quinone;
(e) subjecting the 2,9- and/or the 2,10-disubstituted quinone of formula (IVa) and/or the compound of formula (IVb) to reducing/condensation/aromatization conditions to generate a pentacene compound of formula (Va) and/or a pentacene compound of formula (Vb);

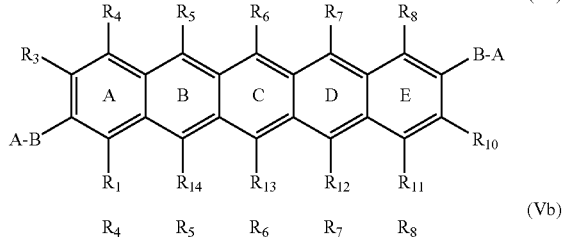

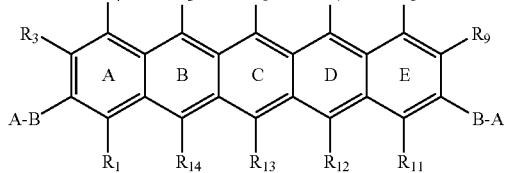

substituted at least in the 2 position, and one of the 9 or 10 positions, wherein the substitutents from $R_1$ to $R_{14}$ are each independently selected from the group consisting of hydrogen, alkyl, alkenyl, alkynyl, aryl, a heterocycle, an electron-withdrawing group, a conjugated electron-withdrawing group, dicyanomethyl, halo, trifluoromethylsulfonyl, alkoxy, aryloxy, amine, haloalkyl, trialkylsilyl, trialkylsilylalkynyl, a thienyl group and a perfluorothienyl group that is unsubstituted or substituted with an alkyl, perfluoroalkyl, alkenyl, alkynyl, halo, haloalkyl, trialkylsilyl, trialkylsilylalkynyl, or a combination thereof;

f) subjecting the 2,9- and/or the 2,10-disubstituted quinone of formula (IVa) and/or the compound of formula (IVb) to reducing/condensation/aromatization conditions to generate a pentacene of formula (V);

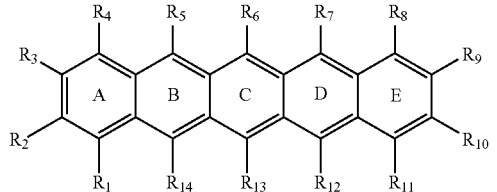

wherein $R_2$, and one of $R_9$ or $R_{10}$ are A-B, and each remaining R group is independently selected from the group consisting of hydrogen, alkyl, alkenyl, alkynyl, aryl, a heterocycle, an electron-withdrawing group, a conjugated electron-withdrawing group, dicyanomethyl, halo, trifluoromethylsulfonyl, alkoxy, aryloxy, amine, haloalkyl, trialkylsilyl, trialkylsilylalkynyl, a thienyl group and a perfluorothienyl that is unsubstituted or substituted with an alkyl, perfluoroalkyl, alkenyl, alkynyl, halo, haloalkyl, trialkylsilyl, trialkylsilylalkynyl, or a combination thereof;

wherein if two or more of steps (c), (d), (e) and (f) occur, then the steps may be performed in any order.

* * * * *